United States Patent
Zee et al.

(10) Patent No.: US 6,255,517 B1
(45) Date of Patent: Jul. 3, 2001

(54) THYMOL DERIVATIVES HAVING ANTI-TUMOR ACTIVITY, AND ANTI-CANCER AGENT COMPRISING THE SAME

(75) Inventors: Ok Pyo Zee, 103-1001, Hyundai Apt. 431, Doryong-dong, Yusung-ku, Daejeon 305-340; Young Hoon Jung, Kwachon; Kang Ro Lee, Suwon; Hyung In Moon, Seoul; Hyung Geun Baek, Kimcheon; Min Jung Lee; Dae Keun Kim, both of Chunrabuk-do, all of (KR)

(73) Assignee: Ok Pyo Zee, Daejon (KR)

( * ) Notice: Subject to any disclaimer, the term of this patent is extended or adjusted under 35 U.S.C. 154(b) by 0 days.

(21) Appl. No.: 09/418,988

(22) Filed: Oct. 14, 1999

(30) Foreign Application Priority Data

Oct. 22, 1998 (KR) .................................................. 98-44341

(51) Int. Cl.[7] ........................ A61K 31/255; C07C 309/73
(52) U.S. Cl. ............................. 558/58; 514/518; 560/20; 560/106; 560/109; 560/144
(58) Field of Search ..................................... 549/555, 557; 558/58; 560/20, 106, 109, 144; 514/518

(56) References Cited

PUBLICATIONS

STN International, CAPLUS Database, Chemical Abstracts Service, (Columbus, Ohio), Accession No. 1982:177897; Bohlmann, F. et al. Phytochemistry 20(10), 2375–8 (1981).*
STN International, CAPLUS Database, Chemical Abstracts Service, (Columbus, Ohio), Accession No. 1984:626858; Delle Monache, G. et al. Phytochemistry 23(9), 1947–50 (1984).*
STN International, CAPLUS Database, Chemical Abstracts Service, (Columbus, Ohio), Accession No. 1995:997335; Yasohara, Y. et al. WO 9528374 (Oct. 1995).*

F. Bohlmann et al., "Neue thymol–erivate aus arnica amplexicaulis", *Tetrahedron Letters*, No. 28, pp. 2827–2828, (1972).

F. Bohlmann et al., "Synthese von 10–acetoxy–8, 9–epoxythymol–isobutyrat", *Chem. Ber.* 109, pp. 2969–2971, (1976).

E. stanoeva et al., "Stereochemie der 3,4–disubstituierten 1,2,3,4–tetrahydro–isochinoline", *Cham. Ber.* 109, pp. 2972–2973, (1976).

C.M. Passreiter et. al., "10–acetoxy–9–chloro–8, 9–dehydrothymol and further thymol derivatives from arnica sachalinensis", *Phytochemistry*, vol. 49, No. 3, pp. 777–781, (1998).

F. Bohlmann et. al., "Uber einige Thymolderivate aus Gaillardia–und Helenium–Arten", *Chem. Ber.* 102, pp. 864–871, (1969).

* cited by examiner

*Primary Examiner*—Robert W. Ramsuer
(74) *Attorney, Agent, or Firm*—Nath & Associates PLLC; Gary M. Nath; Jerald L. Meyer

(57) ABSTRACT

The present invention relates to a thymol derivative represented by following Chemical Formula 1, pharmaceutically acceptable salts or esters thereof, and anti-cancer agents comprising the same as an active ingredient.

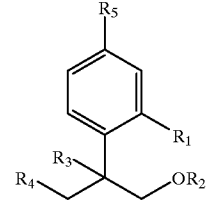

2 Claims, No Drawings

THYMOL DERIVATIVES HAVING ANTI-TUMOR ACTIVITY, AND ANTI-CANCER AGENT COMPRISING THE SAME

FIELD OF THE INVENTION

The present invention relates to a thymol derivative represented by following Chemical Formula 1:

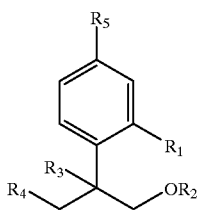

wherein, $R_1$ is a hydroxy group which may be protected with acetyl group or isobutyryl group, methyl group or —$OR_6$ ($R_6$ is benzyl, 4-nitrobenzyl, 4-methyl benzyl, 4-toluenesulfonyl or 4-methoxybenzyl); $R_2$ represents hydrogen, acetyl, isobutyryl, palmitoyl, benzoyl, 4-nitrobenzoyl, 4-methylbenzoyl, phenylacetyl, 4-nitrophenylacetyl, 4-fluorophenylacetyl, 4-methoxyphenylacetyl, methanesulfonyl, 4-methoxybenzenesulfonyl, 4-nitrobenzenesulfonyl, 4-fluorobenzenesulfonyl, o-toluenesulfonyl, 2-nitro-o-toluenesulfonyl or p-toluenesulfonyl; $R_3$ and $R_4$ together forms an epoxy group, diol or olefin; and $R_5$ represents a hydroxy group which may be protected by acetyl group or isobutyryl group, methyl group or hydrogen; and pharmaceutically acceptable salts or esters thereof, and anti-cancer agents comprising the same as an active component.

BACKGROUND OF THE INVENTION

The compound represented by Chemical Formula 38, which is a mother compound of a thymol derivative, was extracted from long tabacco grass (*Carpesium divaricatum* S.). It was firstly isolated and identified by Ferdinand et al. in 1961 (Chem. Ber., 102, 864–871, 1969). The intermediates of thymol were synthesized by Baliman, et al. (Tetrahedron Lett., 20, 2827–2828, 1972).

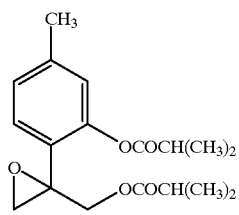

These thymol derivative are compounds of monoterpene derivatives, and it has been reported that terpene type compounds including monoterpenes generally show anti-tumor activity (The Journal of Biological Chemistry, 266 (26), 17679–17685, Carcinogenesis 13(7), 1261–1264). The researches on the pharmacological mechanism of these compounds and developments for anti-cancer agents based on such researches have been actively performed up to the present.

SUMMARY OF THE INVENTION

As a result of intensive studies to develop compounds having excellent anti-tumor activity, the present inventors synthesized various thymol derivative of the present invention by using m-cresol and 2,4-dihydroxyacetophenone as starting material, and found that the compounds has excellent anti-tumor activity.

The present invention relates to a thymol derivative represented by following Chemical Formula 1:

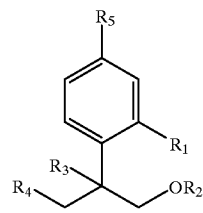

wherein, $R_1$ is a hydroxy group which may be protected with acetyl group or isobutyryl group, methyl group or —$OR_6$ ($R_6$ is benzyl, 4-nitrobenzyl, 4-methyl benzyl, 4-toluenesulfonyl or 4-methoxybenzyl); $R_2$ represents hydrogen, acetyl, isobutyryl, palmitoyl, benzoyl, 4-nitrobenzoyl, 4-methylbenzoyl, phenylacetyl, 4-nitrophenylacetyl, 4-fluorophenylacetyl, 4-methoxyphenylacetyl, methanesulfonyl, 4-methoxybenzenesulfonyl, 4-nitrobenzenesulfonyl, 4-fluorobenzenesulfonyl, o-toluenesulfonyl, 2-nitro-o-toluenesulfonyl or p-toluenesulfonyl; $R_3$ and $R_4$ together forms an epoxy group, diol or olefin; and $R_5$ represents a hydroxy group which may be protected by acetyl group or isobutyryl group, methyl group or hydrogen; pharmaceutically acceptable salts and esters thereof, and anti-cancer agents comprising the same as the active component.

DETAILED DESCRIPTION OF THE INVENTION

Hereinafter, the processes for preparing the compounds represented by Chemical Formula 1 are more specifically described by referring to the reaction schemes.

Method 1

As can be seen from following Scheme 1, the phenolic hydroxyl group of compound of Chemical Formula 2, as the starting material, is acetylated with acetyl chloride to give compound of Chemical Formula 3, which is then subjected to Fries reaction to obtain compound of Chemical Formula 4 wherein acetyl group has been introduced. By using methyl magnesium bromide, compound of Chemical Formula 5 is formed therefrom. Then, the phenolic hydroxyl group is protected by using acetic anhydride, and the tertiary hydroxyl group is simultaneously removed to give compound of Chemical Formula 6. The ester group of compound (6) is hydrolyzed to give compound of Chemical Formula 7, of which the phenolic hydroxyl group is then subjected to esterification by using isobutyric acid, to obtain compound of Chemical Formula 8. Then, a hydroxyl group is introduced to the allylic position of the double bond by using selenium dioxide as a catalyst, to form compound of Chemical Formula 9. When various acids are combined with the newly made hydroxyl group, various compounds represented by Chemical Formula 10 are obtained. The compound (10) is then subjected to epoxidation reaction to provide desired compound of Chemical Formula 11.

Scheme 1.

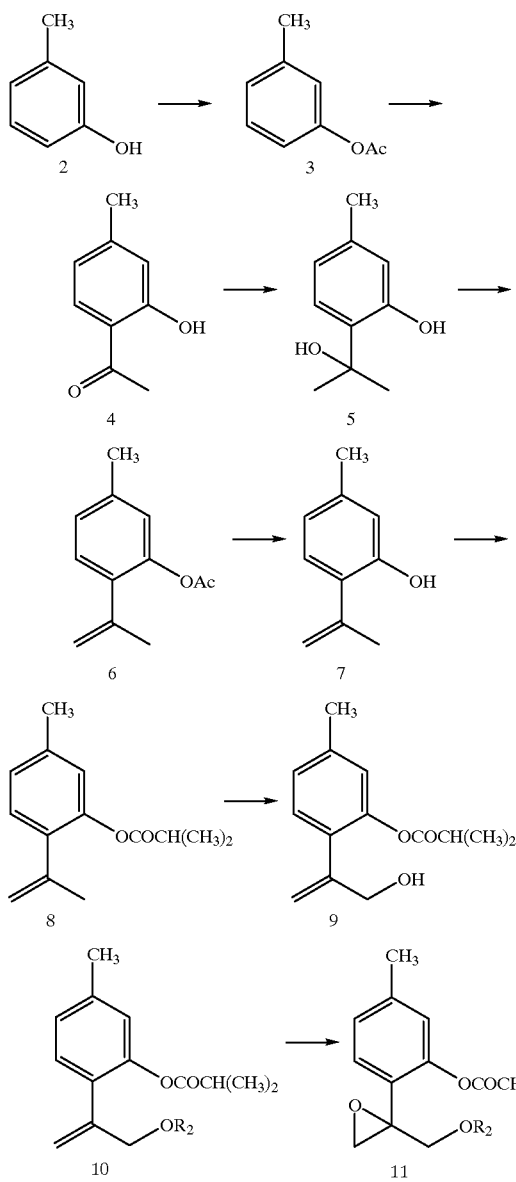

Method 2

As can be seen from following Scheme 2, a hydroxyl group is introduced to the allylic position of the double bond of compound (6) obtained from Method 1, by using selenium dioxide as a catalyst, to form compound of Chemical Formula 12. When various acids are combined with the newly made hydroxyl group, various compounds represented by Chemical Formula 13 are obtained. The compound (13) is then subjected to epoxidation reaction to provide desired compound of Chemical Formula 14.

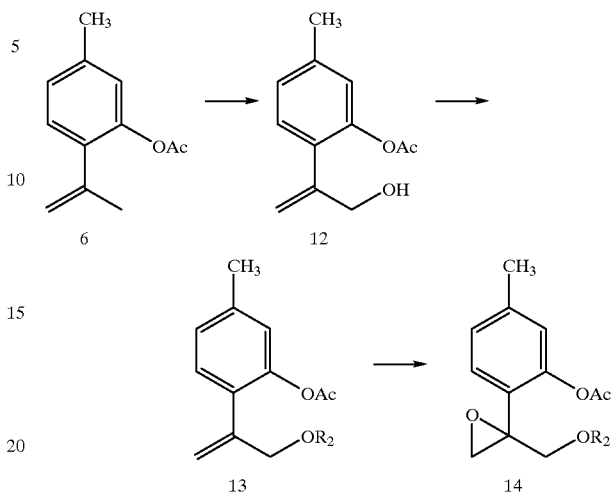

Method 3

As can be seen from following Scheme 3, a compound (13), which was obtained as an intermediate from Method 2, is oxidized with osmium tetraoxide to provide a compound represented by Chemical Formula 15.

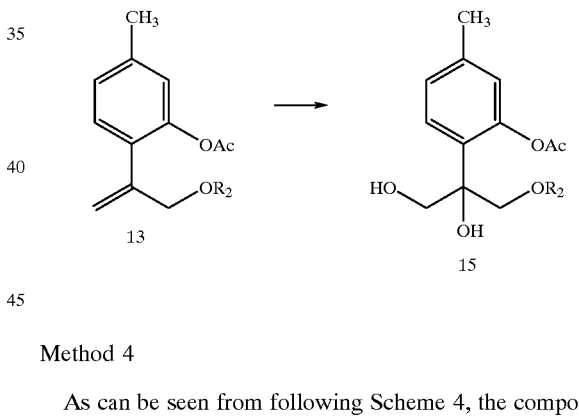

Method 4

As can be seen from following Scheme 4, the compound of Chemical Formula 3 obtained from Method 1, as the starting material, is subjected to Fries reaction to obtain compound of Chemical Formula 16 of which the para position is acetylyzed. By using methyl magnesium bromide, compound of Chemical Formula 17 is formed therefrom. Then, the phenolic hydroxyl group of compound (17) is acetylated by using acetic anhydride, and the tertiary hydroxyl group is simultaneously removed to give compound of Chemical Formula 18. Then, a hydroxyl group is introduced to the allylic position of compound (18) by using selenium dioxide as a catalyst, to form compound of Chemical Formula 19. When various acids are combined with the newly made hydroxyl group, various compounds represented by Chemical Formula 20 are obtained. The compound (20) is subjected to epoxidation reaction to provide desired compound represented by Chemical Formula 21.

Scheme 4

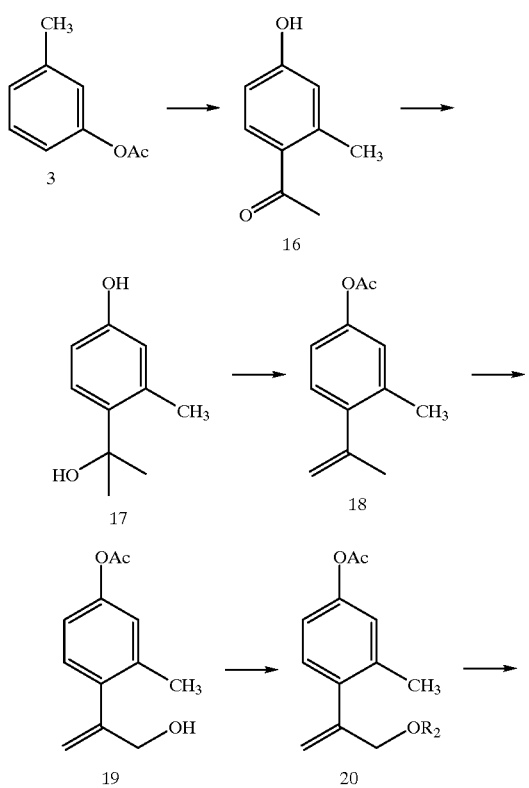

Method 5

As can be seen from following Scheme 5, the compound of Chemical Formula 23 is prepared, from the compound of Chemical Formula 22, by using methyl magnesium bromide. Then, the phenolic hydroxyl group of thus obtained compound (23) is acetylated by using acetic anhydride, and the tertiary hydroxyl group is simultaneously removed to give compound of Chemical Formula 24. Then, a hydroxyl group is introduced to the allylic position of the double bond of the compound (24) by using selenium dioxide as a catalyst, to form compound of Chemical Formula 25. When various acids are combined with the newly made hydroxyl group, various compounds represented by Chemical Formula 26 are obtained. The compound (26) is subjected to epoxidation reaction to provide desired compound represented by Chemical Formula 27.

Scheme 5

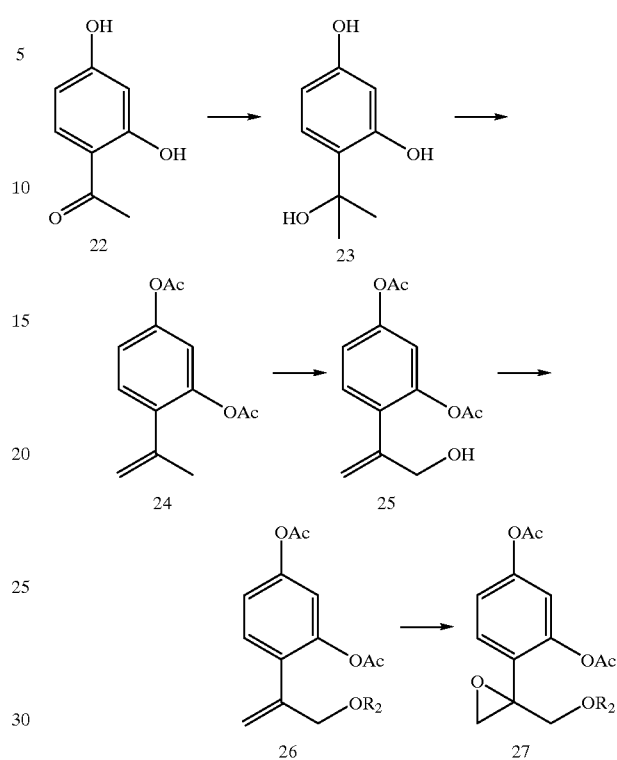

Method 6

As can be seen from following Scheme 6, the compound of Chemical Formula 29 is prepared, from the compound of Chemical Formula 28, by using methyl magnesium bromide. Then, the phenolic hydroxyl group of thus obtained compound (29) is acetylated by using acetic anhydride, and the tertiary hydroxyl group is simultaneously removed, to give compound of Chemical Formula 30. Then, a hydroxyl group is introduced to the allylic position of the double bond of the compound (30) by using selenium dioxide as a catalyst, to form compound of Chemical Formula 31. When various acids are combined with the newly made hydroxyl group, various compounds represented by Chemical Formula 32 are obtained. The compound (32) is then subjected to epoxidation reaction to provide desired compound represented by Chemical Formula 33.

Scheme 6

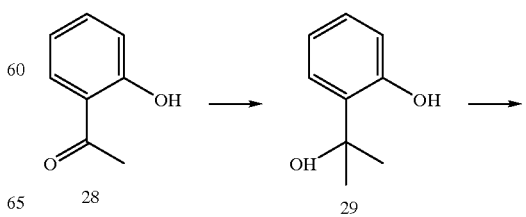

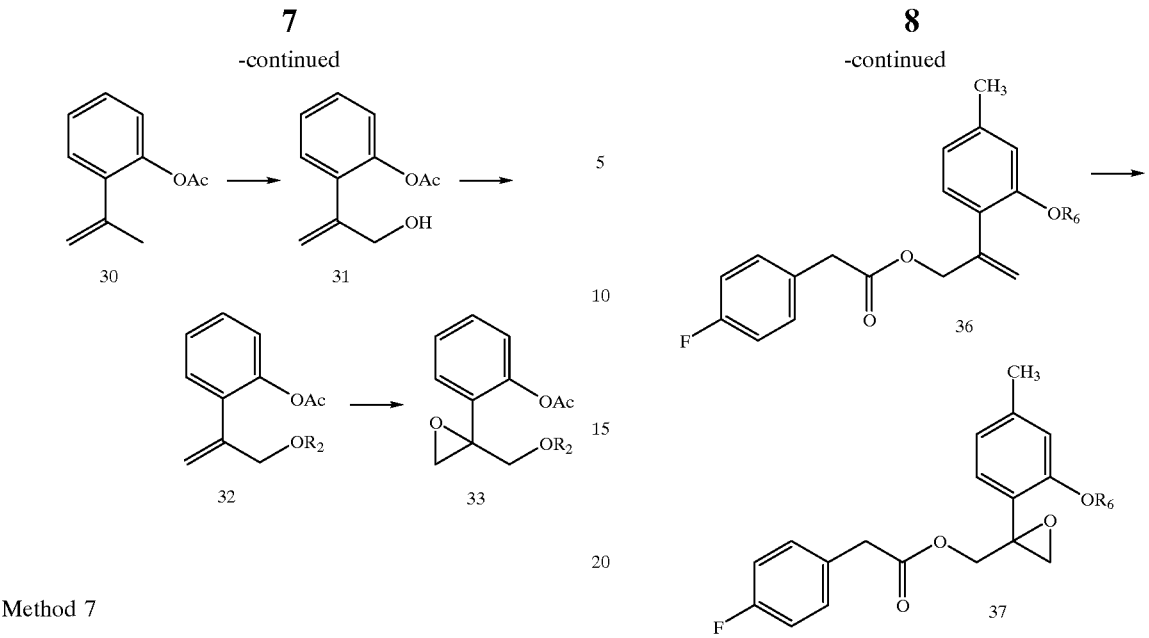

Method 7

As can be seen from following Scheme 7, the compound of Chemical Formula 34 is prepared, from the compound of Chemical Formula 13, by using potassium cyanide. Then, the phenolic hydroxyl group of thus obtained compound (34) is subjected to alkylation by using various alkyl halide in the presence of potassium carbonate and quaternary ammonium salt, to provide corresponding compound represented by Chemical Formula 35.

Then, various acids are combined with the hydroxyl group of compound (35) to give various compounds represented by Chemical Formula 36, which is subjected to epoxidation reaction to provide desired compound represented by Chemical Formula 37.

Scheme 7

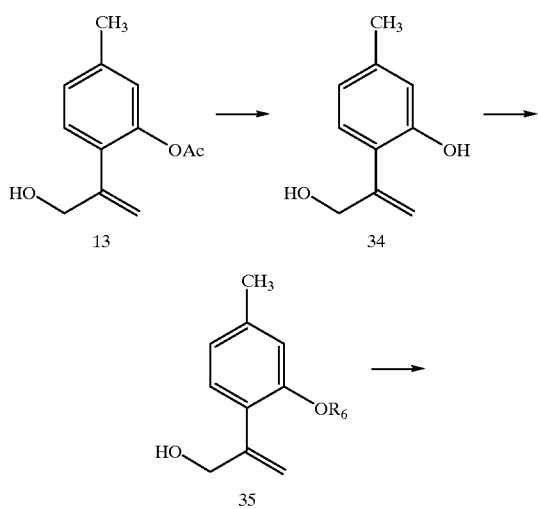

(wherein, $R_6$ represents benzyl, 4-nitrobenzyl, 4-methylbenzyl, 4-toluenesulfonyl or 4-methoxybenzyl.)

The thymol derivative according to the present invention and pharmaceutically acceptable salts or esters thereof can be effectively used as an anti-cancer agent.

The anti-cancer agent according to the present invention may be prepared in an appropriate formulation for oral administration or parenteral administration by means of a conventional formulational process. In case of oral administration, the preparation may be in the form of tablets, capsules, powder, granules, syrup, liquid, elixir, or the like. In case of parenteral administration, the preparation may be in the form of peritoneal, subcutaneous, intramuscular or transcutaneous injection.

The compound represented by Chemical Formula 1 according to the present invention can be administered in an amount of 0.1 mg~2.5 g/kg of body weight per day, preferably 0.2 mg~2.0 mg/kg based on the active component in the early stage. However, the dose may be altered depending on the condition of requirement for the patient, condition of symptom, or the type of compound employed.

PREFERRED EMBODIMENTS OF THE INVENTION

The present invention is now described with reference to Examples and Experimental Examples. However, it should be noted that these examples are intended to be illustrative in nature only, and are not intended to limit or restrict the scope of this invention in any way.

EXAMPLE 1

Preparation of 3-acetoxytoluene (3)

Meta-cresol (1 g, 9.0 mmol) and acetic anhydride (1.1 g, 10.8 mmol) were mixed in the presence of pyridine (3 ml) as a base at 0° C., and gradually heated to room temperature. After 30 minutes, 10~15 ml of water is added thereto, and the mixture was neutralized by adding 1N HCl (30 ml) in three portions. The resultant mixture was extracted with organic solvent, washed, dried and purified by using column chromatography (eluent: hexane/ethyl acetate=6/1) to obtain 1.3 g (96%) of compound (3).

EXAMPLE 2
Preparation of 2-hydroxy-4-methylacetophenone(4)

In a three-necked flask equipped with a thermometer and a condenser, 3-acetoxytoluene (300 mg, 2 mmol) and aluminum chloride (333 mg, 2.5 mmol) were charged, and the mixture was vigorously stirred. Then the temperature was maintained at 90° C. When all the aluminum chloride was dissolved, the mixture was rapidly heated to 120° C., and then slowly heated to 140° C. After standing for 10 minutes, the thermometer and condenser were removed, ice (1.2 g) and concentrated hydrochloric acid (0.75 ml) were added thereto, and the mixture was extracted with organic solvent, washed and dried. Purification through column chromatography (eluent: hexane/ethyl acetate=8/1) gave 270 mg (89%) of compound (4).

EXAMPLE 3
Preparation of 8-hydroxythymol(5)

To a solution of methyl magnesium bromide (5.3 g, 45 mmol) in ether (15 ml), a solution of compound (2) (4.5 g, 30 mmol) in ether (10 ml) was slowly added dropwise at −78° C. After the addition was completed, the solution was slowly heated to room temperature, and stirred for 1 hour. The solution was then cooled to 0° C., and saturated aqueous solution of ammonium chloride (50 ml) was slowly added dropwise. The reaction solution was extracted with organic solvent was washed, dried, and purified by using column chromatography (eluent: hexane/ethyl acetate=8/1) to obtain 4.5 g (90%) of compound (5).

EXAMPLE 4
Preparation of 8,9-dehydrothymol acetate (6)

A solution of compound(5) (1.1 g, 6.4 mmol) was dissolved in acetic anhydride (1.2 ml, 12.7 mmol), stirred for 5 minutes, and refluxed under reflux for 5 hours. The reaction mixture was diluted with water, extracted with organic solvent, dried, and purified by column chromatography (eluent: hexane/ethyl acetate=10/1) to obtain 1 g (83%) of compound (6).

EXAMPLE 5
Preparation of 8,9-dehydrothymol (7)

Compound (6) (1.5 g, 7.9 mmol) was dissolved in methanol (50 ml), and the mixture was stirred for 5 minutes. Potassium cyanide (0.26 g, 3.9 mmol) was added thereto, and the resultant mixture was stirred for 12 hours. After removing the solvent under reduced pressure, the residue was diluted with water, and extracted with organic solvent. The extract was washed, dried and purified on column chromatography (eluent: hexane/ethyl acetate=6/1) to obtain 1.1 g (80%) of compound (7).

EXAMPLE 6
Preparation of 8,9-dehydrothymol isobutyrate (8)

Compound (7) (1.4 g, 9.5 mmol) was dissolved in methylene dichloride (20 ml), and triethyl amine (2.9 g, 4 ml, 28.5 mmol) was slowly added dropwise. The reaction solution was stirred for 5 minutes, and isobutyl chloride (1.2 g, 1.5 ml, 4.8 mmol) was then slowly added thereto over 5 minutes. The reaction mixture was stirred for 4 hours, and the residue was diluted with water, and extracted with organic solvent. The extract was washed, dried and purified by using column chromatography (eluent: hexane/ethyl acetate=8/1) to obtain 1.7 g (85%) of compound (8).

EXAMPLE 7
Preparation of 8,9-dehydro-10-hydroxythymol isobutyrate (9)

Selenium dioxide (530 mg, 4.8 mmol) was dissolved in dry methylene dichloride (50 ml), and t-butyl hydroperoxide (3.9 ml) was slowly added dropwise thereto. The reaction solution was stirred for 1 hour, and then compound (8) (2.1 g, 9.6 mmol) was slowly added dropwise over 10 minutes. After stirring the reaction solution for 20 hours, benzene (20 ml) was added thereto. Methylene dichloride was removed under reduced pressure, and the residue was dissolved in ether (50 ml). The organic layer (10 ml) was washed four times with 10% potassium hydroxide solution. In order to remove excess t-butyl hydroperoxide, ether was evaporated under reduced pressure, and the residue was dissolved in cooled acetic acid (10 ml). Excess methyl sulfide (20 ml) was slowly added dropwise, and the resultant solution was stirred for 4 hours at a temperature of 25 to 30° C. The reaction solution was neutralized with 20% potassium carbonate at 0° C., extracted with organic solvent, dried and purified by column chromatography (hexane/ethyl acetate= 8/1) to obtain 0.9 g (40%) of pure compound (9), and to recover 1 g (48%) of compound (8).

EXAMPLE 8
Preparation of 10-isobutyryloxy-8,9-dehydrothymol isobutyrate (10)

Compound (9) (43 mg, 0.18 mmol) was dissolved in dry methylene dichloride (20 ml), and dicyclohexyl dicarbodiimide (69 mg, 0.33 mmol), dimethylaminopyridine (12 mg, 0.10 mmol) and isobutyric acid (1 9 mg, 0.22 mmol) were subsequently added. After stirring the reaction solution for 2 hours, the organic layer was washed with water and saturated brine, dried over anhydrous magnesium sulfate, and purified by using column chromatography (eluent: hexane/ ethyl acetate=8/1), to obtain 45 mg 80%) of pure compound (10).

EXAMPLE 9
Preparation of 10-isobutyryloxy-8,9-epoxythymol isobutyrate (11)

Acidity of a solution of compound (10) (50 mg, 0.16 mmol) dissolved in methylene dichloride (20 ml) was adjusted at pH 8 to 9 by using 0.4 M sodium hydrogen carbonate. A small amount of m-chloroperbenzoic acid was added thereto, and stirred for 30 minutes. Then, m-chloroperbenzoic acid (70 mg, 0.40 mmol) was added to the reaction solution, and the resultant mixture was stirred for 24 hours. When the reaction was completed, the organic layer was washed with water and saturated brine, dried over anhydrous magnesium sulfate, and purified by using column chromatography (eluent: hexane/ethyl acetate=8/1), to obtain 40 mg (76%) of pure compound (11).

IR (neat): 1770, 1750 cm$^{-1}$ $^1$H-NMR (500 MHz, CDCl$_3$): δ 7.26 (d, 2H, J=7.5 Hz), 6.96 (d, 2H, J=7.5 Hz), 6.78 (s, 1H), 4.45 (d, 1H, J=12.0 Hz), 4.11 (d, 1H, J=12.0 Hz), 2.87 (d, 1H, J=5.0 Hz), 2.79 (m, 1H), 2.63 (d, 1H, J=5.0 Hz), 2.44 (m, 1H), 2.33 (s, 3H), 1.29–1.20 (m, 12H)

EXAMPLE 10

The same procedure as Example 8 was repeated to obtain the compounds defined by following Table 1.

TABLE 1

| $R_2$ | Substituent | No. |
|---|---|---|
| $R_2$ = aromatic group | Phenylacetyl | (10-1) |
| | 4-methoxyphenylacetyl | (10-2) |
| | 4-fluorophenylacetyl | (10-3) |

The analytical data of the above compounds are shown below:

Compound (10-1): 10-Phenylacetoxy-8,9-methylenethymol isobutyrate $^1$H-NMR (500 MHz, CDCl$_3$): δ 7.36–7.29 (m, 5H), 7.15 (d, 1H, J=7.5 Hz), 7.02 (dd, 1H, J=2, 8.0 Hz), 6.85 (d, 1H, J=1 Hz), 5.23 (d, 1H, J=3.0 Hz), 5.09 (d, 1H, J=3.5 Hz), 4.67 (d, 2H, J=1 Hz), 3.83 (s, 2H), 2.56–2.51 (m, 1H), 2.33 (s, 3H), 1.28–1.26 (m, 3H), 1.15–1.12 (m, 3H)

Compound (10-2): 10-(4-Nitrophenylacetoxy)-8,9-methylenethymol isobutyrate $^1$H-NMR (500 MHz, CDCl$_3$): δ 8.23 (dd, 2H, J=2.0, 7.0 Hz), 7.55 (dd, 2H, J=2.0, 7.0 Hz), 7.16 (d, 1H, J=8.0 Hz), 7.05 (d, 1H, J=8.0 Hz), 6.85 (s, 1H), 5.23 (dd, 1H, J=1.5, 8.0 Hz), 5.08 (dd, 1H, J=1.5, 7.5 Hz), 4.74 (s, 2H), 3.97 (s, 2H), 2.57–2.54 (m, 1H), 2.34 (s, 3H), 1.15–1.13 (m, 6H)

Compound (10-3): 10-(4-Fluorophenylacetoxy)-8,9-methylenethymol isobutyrate $^1$H-NMR (500 MHz, CDCl$_3$): δ 7.34–7.31 (m, 2H), 7.15 (d, 1H, J=8.0 Hz), 7.06–7.03 (m, 3H), 6.84 (s, 1H), 5.23 (dd, 1H, J=1.5, 2.5 Hz), 5.08 (d, 1H, J=1.5 Hz), 4.68 (s, 2H), 3.80 (s, 2H), 2.57–2.52 (m, 1H), 1.59 (s, 3H), 1.14 (d, 6H, J=7.0 Hz))

EXAMPLE 11

The same procedure as Example 9 was repeated to obtain the compounds defined by following Table 2.
Table 2.

| $R_2$ | Substituent | No. |
|---|---|---|
| $R_2$ = aromatic group | Phenylacetyl | (11-1) |
| | 4-nitrophenylacetyl | (11-2) |
| | 4-fluorophenylacetyl | (11-3) |
| $R_2$ = saturated hydrocarbonyl | Isobutyryl | 11 |

The analytical data of the above compounds are shown below:

Compound (11-1): 10-Phenylacetoxy-8,9-epoxythymol isobutyrate $^1$H-NMR (500 MHz, CDCl$_3$): δ 7.43–7.37 (m, 4H), 7.34–7.31 (m, 2H), 7.03 (d, 1H, J=7.5 Hz), 6.88 (s, 1H), 4.40 (d, 1H, J=12.0 Hz), 3.89 (s, 2H), 3.83 (d, 1H, J=12.0 Hz), 2.55 (d, 1H, J=5.5 Hz), 2.51–2.45 (m, 2H), 2.33 (s, 3H), 1.12–1.06 (m, 6H)1

Compound (11-2): 10-(4-Nitrophenylacetoxy)-8,9-epoxythymol isobutyrate $^1$H-NMR (500 MHz, CDCl$_3$): δ 8.26–8.23 (m, 2H), 7.62–7.59 (m, 2H), 7.32 (d, 1H, J=7.5 Hz), 7.07–7.05 (m, 1H), 6.86 (s, 1H), 4.46 (d, 1H, J=12.0 Hz), 4.15 (d, 1H, J=12.5 Hz), 4.07 (s, 2H), 2.83 (d, 1H, J=5.0 Hz), 2.71 (d, 1H, J=5.5 Hz), 2.54–2.49 (m, 1H), 2.34 (s, 3H), 1.13–1.10 (m, 6H)

Compound (11-3): 10-(4-Fluorophenylacetoxy)-8,9-epoxythymol isobutyrate $^1$H-NMR (500 MHz, CDCl$_3$): δ 7.40–7.37 (m, 2H), 7.32 (d, 1H, J=8.0 Hz), 7.09–7.03 (m, 3H), 6.86 (s, 1H), 4.43 (d, 1H, J=12.0 Hz), 3.96 (d, 1H, J=12.0 Hz), 3.88 (s, 2H), 2.65 (d, 1H, J=5.0 Hz), 2.61 (d, 1H, J=5.0 Hz), 2.53–2.47 (m, 1H), 2.34 (s, 3H), 1.12–1.07 (m, 6H)

EXAMPLE 12

Preparation of 8,9-Dehydro-10-hydroxythymol acetate (12)

Selenium dioxide (2.3 g, 20.5 mmol) was dissolved in dry methylene dichloride (100 ml), and t-butyl hydroperoxide (8.2 ml, 82.0 mmol) was slowly added dropwise thereto. The reaction solution was stirred for 1 hour, and then compound (7) (3.9 g, 20.5 mmol) was slowly added dropwise over 10 minutes. After stirring the reaction mixture for 20 hours, benzene (40 ml) was added thereto. Methylene dichloride was removed under reduced pressure, and the residue was dissolved in ether (100 ml). The organic layer was washed four times with 10% potassium hydroxide solution (20 ml). In order to remove excess t-butyl hydroperoxide, ether was evaporated under reduced pressure, and the residue was dissolved in cooled acetic acid (25 ml). Excess methyl sulfide (40 ml) was slowly added dropwise, and the resultant mixture was stirred for 4 hours at a temperature of 25 to 30° C. The reaction solution was neutralized with 20% potassium carbonate at 0° C., and extracted with organic solvent. The extract was washed, dried and purified by column chromatography (hexane/ethyl acetate=8/1) to obtain 1.9 g (45%) of pure compound (12), and to recover 1.6 g (40%) of compound (7).

$^1$H-NMR (500 MHz, CDCl$_3$): δ 7.17 (d, 1H, J=7.5 Hz), 7.02 (d, 1H, J=7.5 Hz), 6.85 (s, 1H), 5.38 (d, 1H, J=1.5 Hz), 5.18 (d, 1H, J=1.5 Hz), 4.79 (s, 2H), 2.31 (s, 3H), 2.14 (s, 3H)

EXAMPLE 13

The same procedure as Example 8 was repeated except for using compound (12) obtained from Example 12, instead of compound (9), to obtain the compounds defined by following Table 3.

TABLE 3

| $R_2$ | Substituent | No. |
|---|---|---|
| $R_2$ = aromatic group | Phenylacetyl | 13-1 |
| | 4-methoxyphenylacetyl | 13-2 |
| | 4-nitrophenylacetyl | 13-3 |
| | 4-fluorophenylacetyl | 13-4 |
| | Benzoyl | 13-5 |
| | 4-methylbenzoyl | 13-6 |
| | 4-nitrobenzoyl | 13-7 |
| $R_2$ = saturated hydrocarbonyl | Acetyl | 13-8 |
| | Isobutyryl | 13-9 |
| | Palmitoyl | 13-10 |

The analytical data of the above compounds are shown below:

Compound (13-1): 10-Phenylacetoxy-8,9-methylenethymol acetate

¹H-NMR (500 MHz, CDCl₃): δ 7.36 (d, 1H, J=2.5 Hz), 7.35–7.30 (m, 1H), 7.14 (d, 1H, J=8.0 Hz), 7.02 (d, 1H, J=8.0 Hz), 6.84 (s, 1H), 5.24 (s, 1H), 5.10 (s, 1H), 4.66 (s, 2H), 3.83 (s, 2H), 2.33 (s, 3H), 2.04 (s, 3H)

Compound (13-2): 10-(4-Methoxyphenylacetoxy)-8,9-methylenethymol acetate

¹H-NMR (500 MHz, CDCl₃): δ 7.28–7.25 (m, 2H), 7.14 (d, 1H, J=7.5 Hz), 7.07–7.02 (m, 1H), 6.84 (s, 1H), 5.26 (d, 1H, J=3.0 Hz), 5.11 (d, 1H, J=2.5 Hz), 4.67 (s, 2H), 3.82 (s, 2H), 2.33 (s, 3H), 2.04 (s, 3H)

Compound (13-3): 10-(4-Nitrophenylacetoxy)-8,9-methylenethymol acetate

¹H-NMR (500 MHz, CDCl₃): δ 8.23 (d, 2H, J=9.0 Hz), 7.55 (d, 2H, J=9.0 Hz), 7.16 (d, 1H, J=7.5 Hz), 7.04 (d, 1H, J=7.5 Hz), 6.84 (s, 1H), 5.25 (d, 1H, J=3.0 Hz), 5.09 (d, 1H, J=3.5 Hz), 4.70 (s, 2H), 3.96 (s, 2H), 2.34 (s, 3H), 2.05 (s, 3H)

Compound (13-4): 10-(4-Fluorophenylacetoxy)-8,9-methylenethymol acetate

¹H-NMR (500 MHz, CDCl₃): δ 7.28 (d, 2H, J=9.0 Hz), 7.14 (d, 1H, J=7.5 Hz), 7.03 (d, 1H, J=7.5 Hz), 6.89 (d, 2H, J=9.0 Hz), 6.84 (s, 1H), 5.29 (d, 1H, J=3.0 Hz), 5.11 (d, 1H, J=3.5 Hz), 4.67 (s, 2H), 3.80 (s, 3H), 3.75 (s, 3H), 2.33 (s, 3H), 2.04 (s, 3H)

Compound (13-5): 10-Benzoxy-8,9-methylenethymol acetate

¹H-NMR (500 MHz, CDCl₃): δ 8.17–8.15 (m, 2H), 7.66–7.62 (m, 1H), 7.53–7.49 (m, 2H), 7.26–7.24 (m, 1H), 7.10–7.08 (m, 1H), 7.01 (s, 1H), 5.37 (d, 1H, J=3.0 Hz), 5.29 (d, 1H, J=3.5 Hz), 4.82 (s, 2H), 2.38 (s, 3H), 1.98 (s, 3H)

Compound (13-6): 10-(4-Methylbenzoxy)-8,9-methylenethymol acetate

¹H-NMR (500 MHz, CDCl₃): δ 8.05–8.03 (m, 2H), 7.31–7.29 (m, 2H), 7.23 (d, 1H, J=8.0 Hz), 7.09–7.06 (m, 1H), 7.0 (m, 1H), 6.84 (s, 1H), 5.36 (s, 1H), 5.28 (s, 1H), 4.82 (s, 2H), 2.45 (s, 3H), 2.38 (s, 3H), 1.98 (s, 3H)

Compound (13-7): 10-(4-Nitrobenzoxy)-8,9-methylenethymol acetate

¹H-NMR (500 MHz, CDCl₃): δ 8.38–8.32 (m, 4H), 7.26 (d, 1H, J=7.5 Hz), 7.14–7.12 (m, 1H), 7.03 (d, 1H, J=1 Hz), 5.36 (d, 1H, J=3.0 Hz), 5.26 (d, 1H, J=3.0 Hz), 4.80 (s, 2H), 2.40 (s, 3H), 1.98 (s, 3H)

EXAMPLE 14

Preparation of 10-(p-Toluenesulfonyloxy)-8,9-methylenethymol acetate (13'-1)

To a solution of triethylamine (80 μl, 0.58 mmol) in ether (5 ml), toluenesulfonyl chloride (133 mg, 0.70 mmol) was added, and compound (12) obtained from Example 12 (100 mg, 0.48 mmol) diluted in ether (5 ml) was added dropwise thereto. The mixture was stirred at room temperature for 1 hour, and extracted with organic solvent, dried, concentrated and purified by using column chromatography (eluent: hexane/ethyl acetate=4/1) to obtain 152 mg (96%) of pure compound (13'-1).

¹H-NMR (500 MHz, CDCl₃): δ 7.69 (dd, 2H, J=2, 8 Hz), 7.27–7.29 (m, 2H), 7.08 (d, 2H, J=7.5 Hz), 7.03–7.05 (m, 1H), 5.21 (dd, 1H, J=1.5, 3 Hz), 4.98 (d, 1H, J=1.5 Hz), 4.62 (t, 2H, J=1 Hz), 2.44 (s, 3H), 2.33 (s, 3H), 2.02 (s, 3H)

EXAMPLE 15

The same procedure as Example 14 was repeated to obtain the compounds defined by following Table 4.

TABLE 4

| R₂ | Substituent | No. |
|---|---|---|
| R₂ = aromatic group | Phenylacetyl | 13'-2 |
| | 4-methoxybenzenesulfonyl | 13'-3 |
| | 4-nitrobenzenesulfonyl | 13'-4 |
| | 4-fluorobenzenesulfonyl | 13'-5 |
| | o-toluenesulfonyl | 13'-6 |
| | 2-nitro-o-toluenesulfonyl | 13'-7 |

The analytical data of the above compounds are shown below:

Compound (13'-2): 10-Methanesulfoxy-8,9-methylenethymol acetate

¹H-NMR (500 MHz, CDCl₃): δ 7.22 (d, 1H, J=7.5 Hz), 7.20 (s, 1H), 7.11 (dd, 1H, J=1, 8 Hz), 5.48 (d, 1H, J=1.5 Hz), 5.35 (d, 1H, J=1 Hz), 4.88 (s, 2H), 3.12 (s, 3H), 2.37 (s, 3H), 2.06 (s, 3H)

Compound (13'-3): 10-(4-Methoxybenzenesulfoxy)-8,9-methylenethymol acetate

¹H-NMR (500 MHz, CDCl₃): δ 7.72 (dd, 2H, J=2, 7 Hz), 7.09 (d, 2H, J=6 Hz), 7.07 (s, 1H), 7.03 (dd, 2H, J=2, 8 Hz), 6.93 (dd, 2H, J=2, 7 Hz), 5.21 (dd, 1H, J=1.5, 3 Hz), 5.00 (d, 1H, J=1 Hz), 4.64 (t, 2H, J=1 Hz), 3.87 (s, 3H), 2.33 (s, 3H), 2.04 (s, 3H)

Compound (13'-4): 10-(4-Nitrobenzenesulfoxy)-8,9-methylenethymol acetate

¹H-NMR (500 MHz, CDCl₃): δ 8.38–8.30 (m, 2H), 8.09–8.00 (m, 2H), 7.14–7.08 (m, 3H), 5.17 (d, 1H, J=1 Hz), 4.94 (d, 1H, J=1 Hz), 4.66 (s, 2H), 2.32 (s, 3H), 2.03 (s, 3H)

Compound (13'-5): 10-(4-Fluorobenzenesulfoxy)-8,9-methylenethymol acetate

¹H-NMR (500 MHz, CDCl₃): δ 7.86–7.82 (m, 2H), 7.20–7.12 (m, 2H), 7.08–7.05 (m, 3H), 5.19 (dd, 1H, J=1, 3 Hz), 4.96 (d, 1H, J=1 Hz), 4.71 (s, 2H), 2.34 (s, 3H), 2.02 (s, 3H)

Compound (13'-6): 10-(o-Toluenesulfoxy)-8,9-methylenethymol acetate

¹H-NMR (500 MHz, CDCl₃): δ 7.45 (dd, 2H, J=2, 4.5 Hz), 7.43–7.40 (m, 3H), 7.17 (d, 1H, J=8 Hz), 7.06 (dd, 1H, J=1, 7.5 Hz), 6.96 (s, 1H), 5.43 (dd, 1H, J=1.5, 3 Hz), 5.29 (d, 1H, J=3 Hz), 4.83 (t, 2H, J=1 Hz), 4.56 (s, 2H), 2.32 (s, 3H), 2.05 (s, 3H)

Compound (13'-7): 10-(2-Nitro-o-toluenesulfoxy)-8,9-methylenethymol acetate

¹H-NMR (500 MHz, CDCl₃): δ 8.09 (d, 1H, J=8 Hz), 7.66 (dd, 2H, J=2, 8 Hz), 7.58–7.62 (m, 1H), 7.18 (d, 1H, J=8 Hz), 7.09 (dd, 2H, J=2, 6 Hz), 5.42 (dd, 1H, J=1.5, 2.5 Hz), 5.28 (d, 1H, J=1.5 Hz), 5.14 (s, 2H), 4.81 (t, 2H, J=1 Hz), 2.34 (s, 3H), 2.06 (s, 3H)

EXAMPLE 16

The same procedure as Example 9 was repeated except for using compound (13) obtained from Example 13, instead of compound (10), to obtain the compounds defined by following Table 5.

TABLE 5

| $R_2$ | Substituent | No. |
|---|---|---|
| $R_2$ = aromatic group | Phenylacetyl | 14-1 |
| | 4-methoxyphenylacetyl | 14-2 |
| | 4-nitrophenylacetyl | 14-3 |
| | 4-fluorophenylacetyl | 14-4 |
| | Benzoyl | 14-5 |
| | 4-methylbenzoyl | 14-6 |
| | 4-nitrobenzoyl | 14-7 |
| $R_2$ = saturated hydrocarbonyl | Acetyl | 14-8 |
| | Isobutyryl | 14-9 |
| | palmitoyl | 14-10 |

The analytical data of the above compounds are shown below:

Compound (14-1): 10-Phenylacetoxy-8,9-epoxythymol acetate $^1$H-NMR (500 MHz, CDCl$_3$): δ 7.42–7.36 (m, 4H), 7.33–7.31 (m, 2H), 7.03 (d, 1H, J=8 Hz), 6.88 (s, 1H), 4.32 (d, 1H, J=12.5 Hz), 3.88 (d, 1H, J=11.0 Hz), 3.86 (s, 2H), 2.56 (d, 1H, J=5.0 Hz), 2.53 (d, 1H, J=5.0 Hz), 2.32 (s, 3H), 1.98 (s, 3H)

Compound (14-2): 10-(4-Methoxyphenylacetoxy)-8,9-epoxythymol acetate $^1$H-NMR (500 MHz, CDCl$_3$): δ 7.33–7.26 (m, 3H), 7.04 (d, 1H, J=8.0 Hz), 6.90 (dd, 2H, J=2.0, 7.0 Hz), 6.87 (d, 1H, J=1 Hz), 4.34 (d, 1H, J=12.0 Hz), 3.90 (d, 1H, J=12.0 Hz), 3.82 (s, 2H), 3.81 (s, 3H), 2.60 (d, 1H, J=5.0 Hz), 2.58 (d, 1H, J=5.0 Hz), 2.34 (s, 3H), 1.99 (s, 3H)

Compound (14-3): 10-(4-Nitrophenylacetoxy)-8,9-epoxythymol acetate $^1$H-NMR (500 MHz, CDCl$_3$): δ 8.25 (d, 2H, J=8.5 Hz), 7.60 (d, 2H, J=8.0 Hz), 7.32 (d, 1H, J=8.0 Hz), 7.03 (d, 1H, J=8 Hz), 6.88 (s, 1H), 4.39 (d, 1H, J=12.5 Hz), 4.16 (d, 1H, J=12.5 Hz), 4.05 (s, 2H), 2.84 (d, 1H, J=5.0 Hz), 2.71 (d, 1H, J=5.0 Hz), 2.34 (s, 3H), 2.02 (s, 3H)

Compound (14-4): 10-(4-Fluoropheylacetoxy)-8,9-epoxythymol acetate $^1$H-NMR (500 MHz, CDCl$_3$): δ 7.39–7.36 (m, 2H), 7.33 (d, 1H, J=8.0 Hz), 7.09–7.04 (m, 3H), 6.87 (s, 1H), 4.37 (d, 1H, J=12.0 Hz), 4.00 (d, 1H, J=−12.5 Hz), 3.87 (s, 2H), 2.69 (d, 1H, J=5.0 Hz), 2.62 (d, 1H, J=5.0 Hz), 2.34 (s, 3H), 2.01 (s, 3H)

Compound (14-5): 10-Benzoxy-8,9-epoxythymol acetate $^1$H-NMR (500 MHz, CDCl$_3$): δ 8.21–8.19 (m, 2H), 7.68–7.65 (m, 1H), 7.56–7.52 (m, 2H), 7.42 (d, 1H, J=8.0 Hz), 7.11 (d, 1H, J=8.5 Hz), 7.04 (s, 1H), 4.59 (d, 1H, J=12.5 Hz), 4.18 (d, 1H, J=12.5 Hz), 2.99 (d, 1H, J=5.5 Hz), 2.87 (d, 1H, J=5.5 Hz), 2.39 (s, 3H), 1.96 (s, 3H)

Compound (14-6): 10-(4-Methylbenzoxy)-8,9-epoxythymol acetate $^1$H-NMR (500 MHz, CDCl$_3$): δ 8.09 (d, 2H, J=7.0 Hz), 7.42 (d, 1H, J=8.0 Hz), 7.33 (d, 2H, J=7.5 Hz), 7.10 (d, 1H, J=8.0 Hz), 7.03 (s, 1H), 4.59 (d, 1H, J=12.5 Hz), 4.17 (d, 1H, J=12.0 Hz), 2.98 (d, 1H, J=5.5 Hz), 2.86 (d, 1H, J=5.5 Hz), 2.47 (s, 3H), 2.39 (s, 3H), 1.97 (s, 3H)

Compound (14-7): 10-(4-Nitrobenzoxy)-8,9-epoxythymol acetate $^1$H-NMR (500 MHz, CDCl$_3$): δ 8.42–8.37 (m, 4H), 7.41 (d, 1H, J=8.0 Hz), 7.15 (d, 1H, J=8.0 Hz), 7.06 (s, 1H), 4.56 (d, 1H, J=12.5 Hz), 4.22 (d, 1H, J=12.0 Hz), 2.99 (d, 1H, J=5.5 Hz), 2.86 (d, 1H, J=5.5 Hz), 2.40 (s, 3H), 1.97 (s, 3H)

Compound (14-8): 10-Acetoxy-8,9-epoxythymol acetate $^1$H-NMR (500 MHz, CDCl$_3$): δ 7.35 (d, 1H, J=7.5 Hz), 7.05 (d, 1H, J=7.5 Hz), 6.87 (s, 1H), 4.51 (d, 1H, J=−12.0 Hz), 4.23 (d, 1H, J=12.0 Hz), 3.02 (d, 1H, J=12.0 Hz), 2.80 (d, 1H, J=12.0 Hz), 2.35 (s, 3H), 2.25 (s, 3H), 2.06 (s, 3H)

Compound (14-9): 10-Isobutyryloxy-8,9-epoxythymol acetate $^1$H-NMR (500 MHz, CDCl$_3$): δ7.17 (d, 1H, J=7.5 Hz), 7.03 (d, 1H, J=8.0 Hz), 6.85 (s, 1H), 4.51 (d, 1H, J=12.0 Hz), 4.23 (d, 1H, J=12.0 Hz), 3.02 (d, 1H, J=12.0 Hz), 2.80 (d, 1H, J=12.0 Hz), 2.77 (m, 1H), 2.35 (s, 3H), 2.05 (s, 3H), 1.29–1.25 (m, 6H)

Compound (14-10): 10-Palmitoyloxy-8,9-epoxythymol acetate $^1$H-NMR (500 MHz, CDCl$_3$): δ 7.35 (d, 1H, J=7.5 Hz), 7.05 (d, 1H, J=7.5 Hz), 6.87 (s, 1H), 4.51 (d, 1H, J=12.0 Hz), 4.23 (d, 1H, J=12.0 Hz), 3.02 (d, 1H, J=12.0 Hz), 2.80 (d, 1H, J=12.0 Hz), 2.58 (m, 2H), 2.35 (s, 3H), 2.02 (s, 3H), 1.74 (m, 2H), 1.2 (m, 24H), 0.8 (m, 3H)

EXAMPLE 17

Preparation of 10-(p-toluenesulfoxy)-8,9-epoxythymol acetate (14'-1)

To a solution of compound (13'-1) (53 mg, 0.16 mmol) in a mixed solvent of acetone and water (1:1, 10 ml), potassium hydrogen carbonate (199 mg, 0.32 mmol) and then oxone (324 mg, 3.24 mmol) were added. The mixture was heated to room temperature, and the mixture was stirred for 40 minutes. Saturated solution (aq.) of sodium thiosulfate was added thereto, and the mixture was extracted with ether, and concentrated. The concentrated reaction mixture was dissolved in a mixed solvent of acetic acid, tetrahydrofuran and water (3:1:1), and the resultant solution was stirred at room temperature for 30 minutes. To the solution, saturated sodium hydrogen carbonate was added, and the mixture was extracted with ethyl acetate washed, dried, concentrated and purified by using column chromatography (eluent: hexane/ethyl acetate=3/1) to obtain 39.3 mg (71%) of pure compound (14'-1).

Compound (14'-1): 10-(p-Toluenesulfoxy)-8,9-epoxythymol acetate $^1$H-NMR (500 MHz, CDCl$_3$): δ7.81 (d, 2H, J=6.5 Hz), 7.36 (m, 3H), 7.07 (d, 1H, J=7.5 Hz), 6.94 (d, 1H, J=0.5 Hz), 4.62 (d, 1H, J=12.5 Hz), 4.05 (d, 1H, J=12.5 Hz), 2.99 (d, 1H, J=5 Hz), 2.62 (d, 1H, J=5 Hz), 2.48 (s, 3H), 2.30 (s, 3H), 1.97 (s, 3H)

EXAMPLE 18

The same procedure as Example 17 was repeated to obtain the compounds defined by following Table 6.

TABLE 6

| $R_2$ | Substituent | No. |
|---|---|---|
| $R_2$ = aromatic group | Methanesulfonyl | 14'-2 |
| | 4-methoxybenzenesulfonyl | 14'-3 |
| | 4-nitrobenzenesulfonyl | 14'-4 |
| | 4-fluorobenzenesulfonyl | 14'-5 |
| | o-tolenesulfonyl | 14'-6 |
| | 2-nitro-o-toluenesulfonyl | 14'-7 |

The analytical data of the above compounds are shown below:

Compound (14'-2): 10-Methanesulfoxy-8,9-epoxythymol acetate $^1$H-NMR (500 MHz, CDCl$_3$): δ 7.37 (d, 1H, J=7.5 Hz), 7.21 (d, 1H, J=1 Hz), 7.10 (m, 1H), 4.61 (d, 1H, J=12.5 Hz), 4.30 (d, 1H, J=–12.5 Hz), 3.30 (s, 3H), 3.11 (d, 1H, J=5 Hz), 2.93 (d, 1H, J=5 Hz), 2.37 (s, 3H), 2.02 (s, 3H)

Compound (14'-3): 10-(4-Methoxybenzenesulfoxy)-8,9-epoxythymol acetate $^1$H-NMR (500 MHz, CDCl$_3$): δ 7.86 (m, 2H), 7.36 (d, 1H, J=8 Hz), 7.08 (d, 1H, J=8 Hz), 7.03 (m, 2H), 6.93 (s, 1H), 4.64 (d, 1H, J=12.5 Hz), 4.09 (d, 1H, J=12.5 Hz) 3.90 (s, 3H), 3.01 (d, 1H, J=5 Hz), 2.65 (d, 1H, J=5 Hz), 2.30 (s, 3H), 1.98 (s, 3H)

Compound (14'-4): 10-(4-Nitrobenzenesulfoxy)-8,9-epoxythymol acetate $^1$H-NMR (500 MHz, CDCl$_3$): δ 8.43 (d, 1H, J=9 Hz), 8.19 (d, 1H, J=9 Hz), 7.33 (m, 1H), 7.21 (m, 2H), 7.13 (d, 1H, J=6 Hz), 6.91 (s, 1H), 5.32 (d, 1H, J=1.5 Hz), 5.19 (d, 1H, J=1 Hz), 4.59 (d, 1H, J=12.5 Hz), 4.12 (d, 1H, J=12.5 Hz), 3.05 (d, 1H, J=5 Hz), 2.77 (d, 1H, J=5 Hz), 2.09 (s, 3H), 2.02 (s, 3H)

Compound (14'-5): 10-(4-Fluorobenzenesulfoxy)-8,9-epoxythymol acetate $^1$H-NMR (500 MHz, CDCl$_3$): δ 7.99 (m, 2H), 7.38 (d, 1H, J=8 Hz), 7.28 (m, 2H, J=12.5 Hz), 7.10 (m, 1H), 6.89 (d, 1H, J=5.5 Hz), 4.63 (d, 1H, J=12 Hz), 4.10 (d, 1H, J=12.5 Hz), 3.03 (d, 1H, J=5 Hz), 2.71 (d, 1H, J=5 Hz), 2.31 (s, 3H), 1.98 (s, 3H)

Compound (14'-6): 10-(o-Toluenesulfoxy)-8,9-epoxythymol acetate $^1$H-NMR (500 MHz, CDCl$_3$): δ 7.50 (m, 2H), 7.44 (m, 3H), 7.33 (d, 1H, J=8 Hz), 7.05 (d, 1H, J=5 Hz), 6.80 (s, 1H), 4.65 (d, 1H, J=4 Hz), 4.53 (d, 1H, J=12 Hz), 4.00 (d, 1H, J=12 Hz), 2.80 (d, 1H, J=5 Hz), 2.79 (d, 1H, J=5 Hz), 2.28 (s, 3H), 1.99 (s, 3H)

Compound (14'-7): 10-(2-Nitro-o-toluenesulfoxy)-8,9-epoxythymol acetate $^1$H-NMR (500 MHz, CDCl$_3$): δ 8.12 (d, 1H, J=8 Hz), 7.71 (d, 2H, 3.5 Hz), 7.62 (m, 1H), 7.35 (d, 1H, J=7.5 Hz), 7.08 (m, 1H), 6.98 (s, 1H), 5.31 (d, 1H, J=14.5 Hz), 5.25 (d, 1H, J=14 Hz), 4.53 (d, 1H, J=12.5 Hz), 4.13 (d, 1H, J=12 Hz), 2.99 (d, 1H, J=5 Hz), 2.85 (d, 1H, J=4.5 Hz), 2.32 (s, 3H), 2.02 (s, 3H)

EXAMPLE 19

Preparation of 10-isobutyryloxy-8,9-dihydroxythymol acetate (15)

To a mixture of acetone (1.3 ml), t-butanol (0.5 ml) and water (4 ml), 0.25% aqueous solution of osmium tetraoxide (5.0 mg, 2.0 ml, 0.018 mmol) was added, and then 50% aqueous 4-methylmorpholine-N-oxide solution (25.4 mg, 51 μl, 0.22 mmol) was added. Compound (13-9) (50 mg, 0.18 mmol) was added thereto with stirring, and the resultant mixture was stirred at room temperature. After adding sodium thiosulfate, the reaction mixture was diluted with ethyl acetate, and the organic layer was washed, dried and purified by using column chromatography (eluent: hexane/ethyl acetate=15/1), to obtain 36.4 mg(65%) of pure diol compound (15).

$^1$H-NMR (500 MHz, CDCl$_3$): δ 8.68 (d, 1H, J=3 Hz), 6.89 (d, 1H, J=8 Hz), 6.71 (d, 1H, J=1 Hz), 6.64 (d, 1H, J=8 Hz), 4.48–4.42 (m, 4H), 4.19 (s, 1H), 2.58–2.55 (m, 1H), 2.28 (s, 3H), 2.08 (s, 3H), 1.13 (d, 3H, J=7 Hz), 1.12 (d, 3H, J=7 Hz)

EXAMPLE 20

The same procedure as Example 19 was repeated except for using compound (13) obtained from Example 13, instead of compound (13-9), to obtain the compounds defined by following Table 7.

TABLE 7

| R | Substituent | No. |
|---|---|---|
| R$_1$ = acetyl | Phenylacetyl | 15-1 |
| R$_2$ = aromatic group | 4-nitrophenylacetyl | 15-2 |
|  | 4-fluorophenylacetyl | 15-3 |
|  | 4-methoxyphenylacetyl | 15-4 |
|  | Benzoyl | 15-5 |
|  | 4-nitrobenzoyl | 15-6 |
|  | 4-methoxybenzoyl | 15-7 |
| R$_1$ = isobutyryl | 4-fluorophenyl acetyl | 15-8 |
| R$_2$ = aliphatic group | Isobutyryl | 15-9 |

The analytical data of the above compounds are shown below:

Compound (15-1): 10-Phenylacetoxy-8,9-dihydroxythymol acetate $^1$H-NMR (500 MHz, CDCl$_3$): δ 8.57 (s, 1H), 7.32–7.25 (m, 3H), 7.20 (dd, 2H, J=1 Hz, 4 Hz), 6.81 (d, 1H, J=8 Hz), 6.70 (d, 1H, J=1 Hz), 6.63–6.61 (m, 1H), 4.49–4.35 (m, 4H), 4.03 (s, 1H), 3.63 (s, 2H), 2.28 (s, 3H), 2.05 (s, 3H)

Compound (15-2): 10-(4-Nitrophenylacetoxy)-8,9-dihydroxythymol acetate $^1$H-NMR (500 MHz, CDCl$_3$): δ 8.43 (s, 1H), 8.16–8.12 (m, 2H), 7.34–7.27 (m, 2H), 6.78 (d, 1H, J=8 Hz), 6.69 (d, 1H, J=1 Hz), 6.61–6.59 (m, 1H), 4.52–4.39 (m, 4H), 4.02 (s, 1H), 3.73 (s, 2H), 2.28 (s, 3H), 2.08 (s, 3H)

Compound (15-3): 10-(4-Fluorophenylacetoxy)-8,9-dihydroxythymol acetate $^1$H-NMR (500 MHz, CDCl$_3$): δ 8.53 (s, 1H), 7.16–7.13 (m, 2H), 6.99–6.96 (m, 2H), 6.88 (d, 1H, J=8 Hz), 6.70 (d, 1H, J=1 Hz), 6.61 (dd, 1H, J=1.5 Hz, 8 Hz), 4.49–4.39 (m, 4H), 4.04 (s, 1H), 3.59 (s, 2H), 2.28 (s, 3H), 2.06 (s, 3H)

Compound (15-4): 10-(4-Methoxyphenylacetoxy)-8,9-dihydroxythymol acetate $^1$H-NMR (500 MHz, CDCl$_3$): δ 8.58 (s, 1H), 7.11 (dd, 2H, J=2 Hz, 6.5 Hz), 6.84–6.81 (m, 3H), 6.70 (s, 1H), 6.62 (dd, 1H, J=1 Hz, 8 Hz), 4.48–4.35 (m, 4H), 4.03 (s, 1H), 3.80 (s, 3H), 3.57 (s, 2H), 2.28 (s, 3H), 2.05 (s, 3H)

Compound (15-5): 10-Benzoxy-8,9-dihydroxythymol acetate $^1$H-NMR (500 MHz, CDCl$_3$): δ 8.75 (s, 1H), 8.01–7.99 (m, 2H), 7.60–7.56 (m, 1H), 7.46–7.42 (m, 2H), 6.97 (d, 1H, J=8.5 Hz), 6.73 (d, 1H, J=1 Hz), 6.69–6.67 (m, 1H), 4.71–4.66 (m, 2H), 4.55 (s, 2H), 4.36 (s, 1H), 2.28 (s, 3H), 2.05 (s, 3H)

Compound (15-6): 10-(4-Nitrobenzoxy)-8,9-dihydroxythymol acetate $^1$H-NMR (500 MHz, CDCl$_3$): δ 8.53 (s, 1H), 8.29–8.27 (m, 2H), 8.17–8.14 (m, 2H), 6.97 (d, 1H, J=7.5 Hz), 6.74 (s, 1H), 6.69 (dd, 1H, J=1 Hz, 8 Hz), 4.72–4.67 (m, 2H), 4.62–4.56 (m, 2H), 4.23 (s, 1H), 2.29 (s, 3H), 2.09 (s, 3H)

Compound (15-7): 10-(4-Methoxybenzoxy)-8,9-dihydroxythymol acetate $^1$H-NMR (500 MHz, CDCl$_3$): δ 8.83 (s, 1H), 7.97–7.94 (m, 2H), 6.96 (d, 1H, J=7.5 Hz), 6.93–6.90 (m, 2H), 6.73 (d, 1H, J=1 Hz), 6.68–6.66 (m, 1H), 4.69–4.63 (m, 2H), 4.53 (s, 2H), 4.47 (s, 1H), 3.86 (s, 3H), 2.28 (s, 3H), 2.04 (s, 3H)

Compound (15-8): 10-(4-Fluorophenylacetoxy)-8,9-dihydroxythymol isobutyrate $^1$H-NMR (500 MHz, CDCl$_3$): δ 8.58 (s, 1H), 7.17–7.13 (m, 2H), 6.70–6.95 (m, 2H), 6.81 (d, 1H, J=8 Hz), 6.69 (d, 1H, J=1 Hz), 6.60 (dd, 2H, J=1 Hz, 8 Hz), 4.49–4.39 (m, 4H), 4.14 (s, 1H), 3.60 (s, 2H), 2.57–2.51 (m, 1H), 2.28 (s, 3H), 1.09 (m, 6H)

Compound (15-9): 10-(4-Isobutyryloxy)-8,9-dihydroxythymol isobutyrate $^1$H-NMR (500 MHz, CDCl$_3$): δ 8.74 (s, 1H), 6.89 (d, 1H, J=8 Hz), 6.70 (d, 1H, J=1 Hz), 6.66–6.64 (m, 1H), 4.48–4.42 (m, 4H), 4.30 (s, 1H), 2.60–2.54 (m, 2H), 2.28 (s, 3H), 1.15–1.13 (m, 6H)

EXAMPLE 21

Preparation of 2-methyl-4-hydroxyacetophenone (16)

To nitrobenzene (50 g), m-tolyl acetate (3) (10 g, 67 mmol) was added, and then, aluminum chloride (10 g, 75 mmol) was added thereto in small portions. After stirring the reaction solution at room temperature for 24 hours, ice (10 g) and hydrochloric acid (20 ml) were added thereto. The solution was extracted with organic solvent, washed and dried. After removing nitrobenzene by evaporation, the residue was distilled under reduced pressure to obtain 8.0 g (80%) of pure compound (16).

EXAMPLE 22

Preparation of α-methyl-α-(4'-hydroxy-2'-methylphenyl) ethanol (17)

To a solution of methylmagnesium bromide (30 ml, 90 mmol, 3M solution) dissolved in tetrahydrofuran (15 ml), a solution of compound (16) (4.5 g, 30 mmol) dissolved in tetrahydrofuran (10 ml) was slowly added dropwise at −78° C. When the dropping was completed, was slowly heated to −40° C., and stirred for 5 hours. After heating to 0° C., the solution was stirred for one hour, and then, ammonium chloride (50 ml) was slowly added dropwise thereto. The reaction solution was extracted with organic solvent, washed, dried and purified by using column chromatography (eluent: hexane/ethyl acetate=10/1) to obtain 4.0 g (80%) of pure compound (17).

EXAMPLE 23

Preparation of 4-isopropylene-3-methylphenyl acetate (18)

Compound (17) (131 g, 6.6 mmol) was dissolved in acetic anhydride (1.2 ml), and the solution was stirred for 5 minutes, and then refluxed for 5 hours. The reaction solution was extracted with organic solvent, washed, dried and purified by using column chromatography (eluent: hexane/ethyl acetate=15/1) to obtain 1 g (83%) of pure compound (18).

EXAMPLE 24

Preparation of 2-(4'-acetoxy-2'-methylphenyl)-propen-2-ol (19)

Selenium dioxide (88 mg, 0.8 mmol) was dissolved in dry methylene dichloride (20 ml), and t-butyl hydroperoxide (0.6 ml) was slowly added dropwise thereto. The reaction solution was stirred for one hour, and compound (18) (300 mg, 1.6 mmol) was slowly added dropwise thereto, over 10 minutes. After stirring the reaction mixture for 20 hours, benzene (10 ml) was added thereto, and methylene dichloride was removed under reduced pressure. The residue was dissolved in ether (30 ml). The organic layer was washed four times with 10% aqueous potassium hydroxide. In order to remove excess t-butyl hydroperoxide, ether was evaporated under reduced pressure, and the residue was dissolved in cooled acetic acid (10 ml). Excess amount of methyl sulfide (20 ml) was slowly added dropwise thereto, and the resultant solution was stirred for 4 hours at a temperature of 25 to 30° C. The reaction solution was neutralized with 20% potassium carbonate at 0° C., and extracted with organic solvent. The extract was washed, dried and purified by column chromatography (hexane/ethyl acetate=8/1) to obtain 137 mg (42%) of pure compound (19), and to recover 44 mg (50%) of compound (18).

EXAMPLE 25

The same procedure as Example 8 was repeated except for using compound (19) obtained from Example 24, instead of compound (9), to obtain the compounds defined by following Table 8.

TABLE 8

| R$_2$ | Substituent | No. |
|---|---|---|
| R$_2$ = aromatic group | Phenylacetyl | 20 |

The analytical data of the above compounds are shown below:

Compound (20): 2-(4'-acetoxy-2'-methylphenyl)-prop-2-en phenylacetate $^1$H-NMR (500 MHz, CDCl$_3$): δ 7.35 (d, 1H, J=7.5 Hz), 7.05 (d, 1H, J=7.5 Hz), 6.87 (s, 1H), 4.51 (d, 1H, J=12.0 Hz), 4.23 (d, 1H, J=12.0 Hz), 3.02 (d, 1H, J=12.0 Hz), 2.80 (d, 1H, J=12.0 Hz), 2.58 (m, 2H), 2.35 (s, 3H), 2.02 (s, 3H), 1.74 (m, 2H), 1.2 (m, 24H), 0.8 (m, 3H)

EXAMPLE 26

The same procedure as Example 9 was repeated except for using compound (20) obtained from Example 25, instead of compound (10), to obtain the compounds defined by following Table 9.

TABLE 9

| R$_2$ | Substituent | No. |
|---|---|---|
| R$_2$ = aromatic group | Phenylacetyl | 21-1 |
|  | Benzoyl | 21-2 |
| R$_2$ = saturated hydrocarbonyl | isobutyryl | 21-3 |

The analytical data of the above compounds are shown below:

Compound (21-1): 2-(4'-Acetoxy-2'-methylphenyl)-3-phenylacetoxy-1,2-epoxypropane $^1$H-NMR (500 MHz, CDCl$_3$): δ 7.20–7.33 (m, 5H), 7.20 (d, 1H, J=8.0 Hz), 6.88 (d, 1H, J=8.0 Hz), 6.86 (s, 1H), 4.53 (d, 1H, J=12.5 Hz), 4.22 (d, 1H, J=12.5 Hz), 3.04 (d, 1H, J=5.0 Hz), 2.78 (d, 1H, J=5.0 Hz), 2.37 (s, 3H), 2.29 (s, 3H)

Compound (21-2): 2-(4'-Acetoxy-2'-methylphenyl)-3-benzoyloxy-1,2-epoxypropane $^1$H-NMR (500 MHz, CDCl$_3$): δ 7.99 (m, 2H), 7.54–7.58 (m, 1H), 7.42–7.48 (m, 2H), 7.42 (d, 1H, J=8.0 Hz), 6.93 (d, 1H, J=8.0 Hz), 6.92 (s, 1H), 4.72 (d, 1H, J=12.5 Hz), 4.50 (d, 1H, J=12.5 Hz), 3.24 (d, 1H, J=5.0 Hz), 2.91 (d, 1H, J=5.0 Hz), 2.47 (s, 3H), 2.29 (s, 3H)

Compound (21-3): 2-(4'-Acetoxy-2'-methylphenyl)-3-isobutyryloxy-1,2-epoxypropane $^1$H-NMR (500 MHz, CDCl$_3$): δ 7.39 (d, 1H, J=8.0 Hz), 6.90 (d, 1H, J=8.0 Hz), 6.89 (s, 1H), 4.54 (d, 1H, J=12.5 Hz), 4.19 (d, 1H, J=12.5 Hz), 3.14 (d, 1H, J=5.0 Hz), 2.85 (d, 1H, J=5.0 Hz), 2.53 (m, 1H), 2.42 (s, 3H), 2.28 (s, 3H), 1.10–1.22(m, 6H)

EXAMPLE 27
Preparation of α-Methyl-α-(2',4'-dihydroxyphenyl) ethanol (23)

To a solution of methyl magnesium bromide (15 ml, 0.045 mmol, 3M solution) in tetrahydrofuran (15 ml), compound (22) (4.5 g, 0.037 mmol) dissolved in tetrahydrofuran (10 ml) was slowly added dropwise at −78° C. When the dropping was completed, the temperature was slowly raised to −40° C., and the mixture was stirred for 5 hours. After raising the temperature of the reaction mixture to 0° C., the mixture was stirred for one hour, and then, ammonium chloride (50 ml) was slowly added dropwise thereto. The reaction mixture was extracted with organic solvent, washed, dried and purified by using column chromatography (eluent: hexane/ethyl acetate=10/1) to obtain 3.5 g (70%) of pure compound (23).

$^1$H-NMR (60 MHz, CDCl$_3$): δ 7.3 (d, 1H, J=8.5 Hz), 6.8 (d, 1H, J=8.5 Hz), 6.8 (s, 1H), 2.0 (s, 6H)

EXAMPLE 28
Preparation of 2-(2',4'-diacetoxyphenyl)propene (24)

Compound (23) (1.7 g, 0.012 mmol) was dissolved in acetic anhydride (3.3 ml), and the solution was stirred for 30 minutes, and refluxed for four hours. The reaction solution was extracted with organic solvent, washed, dried and purified by using column chromatography (eluent: hexane/ethyl acetate=6/1), to obtain 2 g (85%) of pure compound (24).

$^1$H-NMR (60 MHz, CDCl$_3$): δ 7.3 (d, 1H), 6.8 (d, 1H), 6.8 (s, 1H), 5.1 (d, 1H), 4.9 (d, 1H), 2.2 (s, 3H), 2.1(s, 3H), 2.0 (s, 3H)

EXAMPLE 29
Preparation of 2-(2',4'-diacetoxyphenyl)-propen-2-ol (25)

Selenium dioxide (21 mg, 0.19 mmol) was dissolved in dry methylene dichloride (10 ml), and t-butyl hydroperoxide (0.15 ml) was slowly added dropwise thereto. The reaction solution was stirred for one hour, and compound (24) (90 mg, 0.38 mmol) was slowly added dropwise thereto, over 10 minutes. After stirring the reaction mixture for 20 hours, benzene (5 ml) was added thereto, and methylene dichloride was removed under reduced pressure. The residue was dissolved in ether (20 ml). The organic layer was washed four times with 10% aqueous potassium hydroxide (5 ml). In order to remove excess t-butyl hydroperoxide, ether was evaporated under reduced pressure, and the residue was dissolved in cooled acetic acid (5 ml). Excess amount of methyl sulfide (10 ml) was slowly added dropwise thereto, and the resultant solution was stirred for 4 hours at a temperature of 25 to 30° C. The reaction solution was neutralized with 20% potassium carbonate at 0° C., and extracted with organic solvent. The extract was washed, dried and purified by column chromatography (eluent: hexane/ethyl acetate=6/1) to obtain 137 mg (42%) of pure compound (25), and to recover 44 mg (50%) of compound (24).

$^1$H-NMR (500 MHz, CDCl$_3$): δ 7.3 (d, 1H), 6.8 (d, 1H), 6.8 (s, 1H), 5.5 (d, 1H), 5.3 (d, 1H), 4.9 (s, 2H), 2.2 (s, 3H), 2.0 (s, 3H)

EXAMPLE 30
The same procedure as Example 8 was repeated except for using compound (25) obtained from Example 29, instead of compound (9), to obtain the compounds defined by following Table 10.

TABLE 10

| R$_2$ | Substituent | No. |
|---|---|---|
| R$_2$ = aromatic group | Phenylacetyl | 26-1 |
| | 4-nitrophenylacetyl | 26-2 |
| | 4-fluorophenylacetyl | 26-3 |
| | 4-nitrobenzoyl | 26-4 |
| R$_2$ = saturated hydrocarbonyl | Acetyl | 26-5 |

The analytical data of the above compounds are shown below: Compound (26-1): 2-(2',4'-Diacetoxyphenyl)-prop-2-ene phenylacetate $^1$H-NMR (500 MHz, CDCl$_3$): δ 7.31–7.36 (m, 5H), 7.25 (d, 1H, J=8.5 Hz), 6.98 (d, 1H, J=8.8 Hz), 6.87 (s, 1H), 5.27 (d, 1H, J=3.0 Hz), 5.12 (d, 1H, J=1.0 Hz), 4.65 (s, 2H), 3.81 (s, 2H), 2.27 (s, 3H), 2.02 (s, 3H)

Compound (26-2): 2-(2',4'-Diacetoxyphenyl)-prop-2-ene 4-nitrophenyl acetate $^1$H-NMR (500 MHz, CDCl$_3$): δ 8.21 (d, 2H, J=9.0 Hz), 7.53 (d, 2H, J=9.0 Hz), 7.26 (d, 1H, J=8.5 Hz), 7.01 (d, 1H, J=8.5 Hz), 6.89 (s, 1H), 5.29 (d, 1H, J=1.0 Hz), 5.12 (d, 1H, J=1.0 Hz), 4.70 (s, 2H), 3.96 (s, 2H), 2.27 (s, 3H), 2.02 (s, 3H)

Compound (26-3): 2-(2',4'-Diacetoxyphenyl)-prop-2-ene 4-fluorophenyl acetate $^1$H-NMR (500 MHz, CDCl$_3$): δ 7.45 (d, 1H, J=8.5 Hz), 7.36 (m, 2H), 7.07 (m, 2H), 7.00 (d, 1H, J=8.5 Hz), 6.92 (s, 1H), 5.29 (d, 1H, J=1.0 Hz), 5.11 (s, 1H), 4.67 (s, 2H), 3.79 (s, 2H), 2.28 (s, 3H), 2.04 (s, 3H)

Compound (26-4): 2-(2',4'-Diacetoxyphenyl)-prop-2-ene 4-nitrobenzoate $^1$H-NMR (500 MHz, CDCl$_3$): δ 8.31–8.37 (m, 4H), 7.39 (d, 1H, J=8.5 Hz), 7.08 (d, 1H, J=8.5 Hz), 7.07 (s, 1H), 5.41 (d, 1H, J=1.0 Hz), 5.29 (d, 1H, J=1.0 Hz), 4.80 (s, 2H), 3.79 (s, 2H), 2.28 (s, 3H), 2.04 (s, 3H)

Compound (26-5): 2-(2',4'-Diacetoxyphenyl)-prop-2-ene acetate $^1$H-NMR (500 MHz, CDCl$_3$): δ 7.30 (d, 1H, J=8.5 Hz), 7.00 (d, 1H, J=8.5 Hz), 6.91 (s, 1H), 5.42 (d, 1H, J=1.0 Hz), 5.25 (d, 1H, J=1.0 Hz), 4.81 (s, 2H), 2.30 (s, 3H), 2.26 (s, 3H), 2.06 (s, 3H)

EXAMPLE 31
The same procedure as Example 9 was repeated except for using compound (26) obtained from Example 30, instead of compound (10), to obtain the compounds defined by following Table 11.

TABLE 11

| R$_2$ | Substituent | No. |
|---|---|---|
| R$_2$ = aromatic group | Phenylacetyl | 27-1 |
| | 4-nitrophenylacetyl | 27-2 |
| | 4-fluorophenylacetyl | 27-3 |
| | 4-nitrobenzoyl | 27-4 |
| R$_2$ = saturated hydrocarbonyl | Acetyl | 27-5 |

The analytical data of the above compounds are shown below:

Compound (27-1): 2-(2',4'-Diacetoxyphenyl)-3-phenylacetoxy-1,2-epoxypropane $^1$H-NMR (500 MHz, CDCl$_3$): δ 7.25 (d, 1H, J=8.5 Hz), 7.31–7.38 (m, 5H), 6.98 (d, 1H, J=8.8 Hz), 6.93 (s, 1H), 4.31 (d, 1H, J=12.0 Hz), 3.89 (d, 1H, J=12.0 Hz), 3.87 (s, 2H), 2.57 (d, 1H, J=5.5 Hz), 2.55 (d, 1H, J=5.5 Hz), 2.27 (s, 3H), 1.98 (s, 3H)

Compound (27-2): 2-(2',4'-Diacetoxyphenyl)-3-(4-nitrophenylacetoxy)-1,2-epoxypropane $^1$H-NMR (500 MHz, CDCl$_3$): δ 8.21 (d, 2H, J=9.0 Hz), 7.53 (d, 2H, J=9.0 Hz), 7.26 (d, 1H, J=8.5 Hz), 7.01 (d, 1H, J=8.5 Hz), 6.89 (s, 1H), 4.39 (d, 1H, J=12.5 Hz), 4.17 (d, 1H, J=12.5 Hz), 4.05 (s, 2H), 2.85 (d, 1H, J=5.0 Hz), 2.72 (d, 1H, J=5.0 Hz), 2.28 (s, 3H), 2.03 (s, 3H)

Compound (27-3): 2-(2',4'-Diacetoxyphenyl)-3-(4-fluorophenylacetoxy)-1,2-epoxypropane $^1$H-NMR (500 MHz, CDCl$_3$): δ 7.45 (d, 1H, J=8.5 Hz), 7.36 (m, 2H), 7.07 (m, 2H), 7.00 (d, 1H, J=8.5 Hz), 6.92 (s, 1H), 4.35 (d, 1H, J=12.5 Hz), 4.01 (d, 1H, J=12.5 Hz), 3.86 (s, 2H), 2.70 (d, 1H, J=5.0 Hz), 2.64 (d, 1H, J=5.0 Hz), 2.28 (s, 3H), 2.01 (s, 3H)

Compound (27-4): 2-(2',4'-Diacetoxyphenyl)-3-(4-nitrobenzoxy)-1,2-epoxypropane $^1$H-NMR (500 MHz, CDCl$_3$): δ 8.40 (s, 4H), 7.54 (d, 1H, J=8.5 Hz), 7.11 (d, 1H, J=8.5 Hz), 7.09 (s, 1H), 4.56 (d, 1H, J=12.5 Hz), 4.23 (d, 1H, J=12.5 Hz), 3.02 (d, 1H, J=5.5 Hz), 2.88 (d, 1H, J=5.5 Hz), 2.32 (s, 3H), 1.98 (s, 3H)

Compound (27-5): 2-(2',4'-Diacetoxyphenyl)-3-acetoxy-1,2-epoxypropane $^1$H-NMR (500 MHz, CDCl$_3$): δ 7.48 (d, 1H, J=8.5 Hz), 7.02 (d, 1H, J=8.5 Hz), 6.95 (s, 1H), 4.50 (d, 1H, J=12.5 Hz), 4.28 (d, 1H, J=12.5 Hz), 3.05 (d, 1H, J=5.5 Hz), 2.81 (d, 1H, J=5.5 Hz), 2.34 (s, 3H), 2.29 (s, 3H), 2.03 (s, 3H)

EXAMPLE 32
Preparation of 2-(1-hydroxy-1-methylethyl)-phenol (29)

To a solution of methyl magnesium bromide (6.36 g, 54 mmol) dissolved in ether (20 ml), a solution of compound (28) (5 g, 36.7 mmol) dissolved in ether (15 ml) was slowly added dropwise at −78° C. When the dropping was completed, the mixture was slowly heated to room temperature, and stirred for 1 hour. After cooling the reaction mixture to 0° C., saturated aqueous ammonium chloride (55 ml) was slowly added dropwise thereto. The reaction solution was extracted with organic solvent, washed, dried and purified by using column chromatography (eluent: hexane/ethyl acetate=6/1) to obtain 5.25 g (94%) of compound (29).

$^1$H-NMR (500 MHz, CDCl$_3$): δ 7.34–7.30 (m, 2H), 7.27–7.24 (m, 1H), 7.07 (dd, 1H, J=1, 7 Hz), 5.22 (s, 1H), 5.07 (s, 1H), 2.31 (s, 3H), 2.11 (s, 3H)

EXAMPLE 33
Preparation of 2-isopropenyl phenyl acetate (30)

Compound (29) (3.0 g, 20 mmol) was dissolved in acetic anhydride (3.6 ml, 39 mmol), and the solution was stirred for 5 minutes. After reflux for 5 hours, the reaction solution was diluted with water, and extracted with organic solvent. The extract was washed, dried and purified by using column chromatography (eluent: hexane/ethyl acetate=10/1), to obtain 3.1 g (91%) of pure compound (30).

$^1$H-NMR (500 MHz, CDCl$_3$): δ 9.11 (s, 1H), 7.22–7.18 (m, 1H), 7.13–7.11 (m, 1H), 6.91–6.85 (m, 2H), 2.96 (s, 1H), 1.70 (s, 6H)

EXAMPLE 34
Preparation of 2-(1-hydroxymethylvinyl)phenyl acetate (31)

Selenium dioxide (310 mg, 2.8 mmol) was dissolved in dry methylene dichloride (30 ml), and t-butyl hydroperoxide (2.2 ml) was slowly added dropwise thereto. The reaction solution was stirred for one hour, and compound (30) (1 g, 5.7 mmol) was slowly added dropwise thereto, over 10 minutes. After stirring the reaction solution for 20 hours, benzene (10 ml) was added thereto, and methylene dichloride was removed under reduced pressure. The residue was dissolved in ether (40 ml). The organic layer was washed four times with 10% aqueous potassium hydroxide (10 ml). In order to remove excess t-butyl hydroperoxide, ether was evaporated under reduced pressure, and the residue was dissolved in cooled acetic acid (5 ml). Excess amount of methyl sulfide (10 ml) was slowly added dropwise thereto, and the resultant solution was stirred for 4 hours at a temperature of 25 to 30° C. The reaction solution was neutralized with 20% potassium carbonate at 0° C., and extracted with organic solvent. The extract was washed, dried and purified by column chromatography (eluent: hexane/ethyl acetate=10/1) to obtain 573 mg (53%) of pure compound (31), and to recover 420 mg (42%) of compound (30).

$^1$H-NMR (500 MHz, CDCl$_3$): δ 7.27–7.24 (m, 1H), 7.15 (dd, 1H, J=2, 7.5 Hz), 6.97–6.91 (m, 2H), 6.80 (s, 1H), 5.55 (s, 1H), 5.36 (s, 1H), 4.85 (s, 1H), 2.18 (s, 3H)

EXAMPLE 35
The same procedure as Example 8 was repeated except for using compound (31) obtained from Example 34, instead of compound (9), to obtain the compounds defined by following Table 12.

TABLE 12

| R$_2$ | Substituent | No. |
|---|---|---|
| R$_2$ = aromatic group | Phenylacetyl | 32-1 |
| | 4-nitrophenylacetyl | 32-2 |
| | 4-fluorophenylacetyl | 32-3 |
| | 4-methoxyphenylacetyl | 32-4 |
| | Benzoyl | 32-5 |
| | 4-methylbenzoyl | 32-6 |

The analytical data of the above compounds are shown below:

Compound (32-3): 2-(2'-Acetoxyphenyl)-prop-2-ene 4-fluorophenyl acetate $^1$H-NMR (500 MHz, CDCl$_3$): δ 7.33–7.20 (m, 5H), 7.06–7.02 (m, 3H), 5.27 (dd, 1H, J=1.5, 3 Hz), 5.12 (dd, 1H, J=1.5, 2.5 Hz), 4.68 (s, 2H), 3.81 (s, 2H), 2.04 (s, 3H)

EXAMPLE 36
The same procedure as Example 9 was repeated except for using compound (32) obtained from Example 35, instead of compound (10), to obtain the compounds defined by following Table 13.

TABLE 13

| R$_2$ | Substituent | No. |
|---|---|---|
| R$_2$ = aromatic group | Phenylacetyl | 33-1 |
| | 4-nitrophenylacetyl | 33-2 |

TABLE 13-continued

| R$_2$ | Substituent | No. |
|---|---|---|
| | 4-fluorophenylacetyl | 33-3 |
| | 4-methoxyphenylacetyl | 33-4 |
| | Benzoyl | 33-5 |
| | 4-methylbenzoyl | 33-6 |

The analytical data of the above compounds are shown below:
Compound (33-3): 2-(2'-Acetoxyphenyl)-3-(4-fluorophenylacetoxy)-1,2-epoxypropane
$^1$H-NMR (500 MHz, CDCl$_3$): δ 7.45 (dd, 1H, J=1.5, 8 Hz), 7.39–7.34 (m, 3H), 7.27–7.23 (m, 1H), 7.09–7.05 (m, 3H), 4.39 (d, 1H, J=12 Hz), 4.01 (d, 1H, J=12 Hz), 3.88 (s, 2H), 2.69 (d, 1H, J=5.5 Hz), 2.64 (d, 1H, J=5.5 Hz), 2.00 (s, 3H)

EXAMPLE 37
Preparation of 8,9-dehydro-10-hydroxythymol (34)

To a solution of compound (13) (865 mg, 4.2 mmol) dissolved in absolute methanol (5 ml), potassium cyanide (137 mg, 2.1 mmol) was added, and stirred at room temperature for 12 hours. The reaction mixture was evaporated to dryness, diluted with water, and extracted with organic solvent. The extract was washed, dried and purified by using column chromatography (eluent: hexane/ethyl acetate=2/1), to obtain 630 mg (91%) of pure compound (34).
$^1$H-NMR (500 MHz, CDCl$_3$): δ 7.03 (d, 1H, J=7.5 Hz), 6.75 (d, 1H, J=0.5 Hz), 6.70–6.68 (m, 1H), 5.48–5.47 (m, 1H), 5.38–5.37 (m, 1H), 4.41–4.39 (m, 2H), 2.31 (s, 3H)

EXAMPLE 38
Preparation of 2-(2-(4'-nitrobenzyloxy)-4-methylphenyl)-prop-2-ene-1-ol (35)

To dry acetone (5 ml), potassium carbonate (13 mg, 0.091 mmol), p-nitrobenzyl chloride (16 mg, 0.091 mmol) and quaternary ammonium bromide (2 mg, 0.006 mmol) were added. Compound (34) (10 mg, 0.061 mmol) was added thereto, and the mixture was stirred under reflux for 4 hours. After removing acetone under reduced pressure, the residue was extracted with organic solvent. The extract was washed, dried and purified by using column chromatography (eluent: hexane/ethyl acetate=2/1), to obtain 13 mg (71%) of pure compound (35).
$^1$H-NMR (500 MHz, CDCl$_3$): δ 8.39 (dd, 2H, J=2, 9 Hz), 7.73 (d, 2H, J=8.5 Hz), 7.29 (d, 1H, J=8 Hz), 6.97 (d, 1H, J=7.5 Hz), 6.86 (s, 1H), 5.57 (dd, 1H, J=1.5, 3 Hz), 5.39 (d, 1H, J=0.5 Hz), 5.32 (s, 2H), 4.60 (s, 2H), 2.48 (s, 3H)

EXAMPLE 39
Preparation of (4-fluorophenyl)acetic Acid 2(2-(4'-nitrobenzyloxy)-4-methylphenyl)-allyl Ester (36)

To a solution of compound (35) (28.2 mg, 0.09 mmol) in dry methylene dichloride (10 ml), dicyclohexyl dicarbodiimide (42.8 mg, 0.21 mmol), dimethylaminopyridine (8.1 mg, 0.07 mmol) and 4-fluorophenylacetic acid (21.8 mg, 0.14 mmol) were sequentially added. The reaction solution was stirred for two hours, filtered, and evaporated under reduced pressure to remove the solvent. The residue was extracted with organic solvent, washed, dried and purified by using column chromatography (eluent: hexane/ethyl acetate=4/1), to obtain 30.6 mg (72%) of pure compound (36).

$^1$H-NMR (500 MHz, CDCl$_3$): δ 8.23–8.20 (m, 2H), 7.53 (dd, 2H, J=2, 6.5 Hz), 7.12–6.99 (m, 3H), 6.95–6.92 (m, 2H), 6.78 (dd, 1H, J=2, 7.5 Hz), 6.65 (s, 1H), 5.32 (dd, 1H, J=1.5, 3 Hz), 5.25 (dd, 1H, J=1, 2 Hz), 5.09 (s, 2H), 4.98 (s, 2H), 2.35 (s, 3H)

EXAMPLE 40
Preparation of (4-fluorophenyl)acetic acid 2-(2-(4'-nitrobenzyloxy)-4-methylphenyl)-oxiranemethyl ester (37)

Acidity of a solution of compound (36) (19 mg, 0.04 mmol) dissolved in methylene dichloride (10 ml) was adjusted at pH 8 to 9 by using 0.4 M sodium hydrogen carbonate. A small amount of m-chloroperbenzoic acid was added thereto, and the solution was stirred for 30 minutes. Then, m-chloroperbenzoic acid (9 mg, 0.05 mmol) was added to the reaction solution, and was stirred for 24 hours. When the reaction was completed, the solvent was removed by evaporation under reduced pressure, and the residue was extracted, washed, dried and purified by using column chromatography (eluent: hexane/ethyl acetate=4/1), to obtain 10.9 mg (55%) of pure compound (37).
$^1$H-NMR (500 MHz, CDCl$_3$): δ 8.25 (dd, 2H, J=2, 8.5 Hz), 7.53 (dd, 2H, J=6.5, 8.5 Hz), 7.12–6.99 (m, 3H), 6.95–6.92 (m, 2H), 6.81 (d, 1H, J=8 Hz), 6.78 (d, 1H, J=7 Hz), 6.66 (s, 1H), 5.16 (d, 1H, J=11.5 Hz), 5.09 (d, 1H, J=12 Hz), 4.79 (d, 1H, J=12 Hz), 4,19 (d, 1H, J=11.5 Hz), 3.50 (s, 2H), 3.04 (d, 1H, J=5.5 Hz), 2.80 (d, 1H, J=5 Hz), 2.33 (s, 3H)

EXAMPLE 41
The same procedure as Example 38 was performed to obtain the compounds described in following Table 14.

TABLE 14

| R | Substituent | No. |
|---|---|---|
| R$_6$ = aromatic group | 4-methoxybenzyl | 35-1 |
| | 4-methylbenzyl | 35-2 |
| | 4-toluenesulfonyl | 35-3 |

Compound (35-2): 2-(2-(4'-Methylbenzyloxy)-4-methylphenyl)-prop-2-ene-1-ol
$^1$H-NMR (500 MHz, CDCl$_3$): δ 7.32 (d, 2H, J=7.5 Hz), 7.21 (d, 2H, J=8 Hz), 7.15 (d, 1H, J=7.5 Hz), 6.80 (dd, 2H, J=1.5, 3 Hz), 5.38 (dd, 1H, J=1, 3 Hz), 5.25 (t, 1H, J=1 Hz), 5.04 (s, 2H), 4.41 (d, 2H, J=4 Hz), 2.38 (s, 3H), 2.37 (s, 3H)
Compound (35-3): 2-(2-(4'-Toluenesulfoxy)-4-methylphenyl)-prop-2-ene-1-ol
$^1$H-NMR (500 MHz, CDCl$_3$): δ 7.71 (dd, 2H, J=2, 8 Hz), 7.31 (d, 2H, J=8.5 Hz), 7.13 (d, 1H, J=8 Hz), 7.06 (d, 1H, J=8 Hz), 6.94 (s, 1H), 5.31 (dd, 1H, J=1.5, 3 Hz), 5.01 (d, 1H, J=1 Hz), 4.29 (d, 2H, J=6 Hz), 2.46 (s, 3H), 2.30 (s, 3H)

Experimental Example 1
Anti-Tumor (Cyto-Toxicity) Effect in vitro of the Compound According to the Present Invention
Detection of Cyto-Toxicity The method for detecting cyto-toxicity employed in the present experiment is Sulforhodamin B Bioassay (SRB) method, which was developed by National Cancer Institute (NCI) in the United States in 1989, for the purpose of measuring anti-tumor activity in vitro.

Cultivation of Tumor Cells

The tumor cells used in the experiments via SRB method are listed below:

A549: non small cell lungcarcinoma

SK-OV-3: adenocarcinoma, ovary malignant ascites

SK-MEL-2: malignant melanoma, metastasis to skin of thigh

XF498: central nerve system tumor

HCT15: colon adenocarcinoma

The tumor cells listed above are all human tumor cell-lines, which were distributed from NCI in the United States and subcultured in Korea Chemical Institute. As a culture medium, RPMI 1640 culture medium supplemented with 5% FBS (fetal bovine serum) was used. Cultivation was performed in an 5% $CO_2$ incubator with constant temperature (37° C.) and humidity. The subculture was carried out every three or four days, and a solution of 0.25% tyrosine and 3 mM trans-1,2-diaminocyclohexane-n,n,n,n-tetracetic acid (CDTA) dissolved in PBS (phosphate buffered saline) was used in order to release cells from the surface of the container.

Separately, for detecting the anti-tumor activity, detection of cyto-toxicity was performed by SRB method using human tumor cell-lines such as KHOS-NP and A431, which were subcultured in College of Pharmacy of Woosuk University.

Preparation of Samples

The test compound synthesized according to the present invention was diluted to have a concentration of 30.0 μg/ml, 10.0 μg/ml, 3.0 μg/ml, 1.0 μg/ml, 0.3 μg/ml and 0.1 μg/ml, respectively, and the cyto-toxicity (anti-tumor activity) of the compound was measured. The maximum concentration of the sample was not more than 30.0 μg/ml. In order to prepare the samples for detection, DMSO (dimethylsulfoxide) was used, if necessary. The concentration of DMSO added was not more than 0.5%. Before added to the tumor cells, the sample solution, which was diluted via several steps, is filtered through a Millipore filter. In a sterile condition, the sample for detecting cyto-toxicity was prepared by means of SRB method using human tumor cell-lines such as A549, SK-OV-3, SK-MEL-2, XF498 and HCT15.

Measuring the Activity

The subcultured tumor cells were released from the surface of instrument by using tyrosine-CDTA solution, and then charged on a 96-well flat bottom microplate to make the cell number $5\times10^3$(A549, HCT15), $1\times10^4$(SK-MEL-2, XF498) and $2\times10^4$(SK-OV-3) for each cell. The tumor cells are attached on the bottom by cultivating in a $CO_2$ incubator. After removing the culture medium by using an aspirator, the medium is eliminated by using log dose of six concentrations. To each well, 100 μl of 10% TCA (trichloroacetic acid) is added, and the plate was left for 1 hour at 4° C. to fix the cells on the bottom surface of the plate.

Then, the plate was washed with distilled water 5–6 times to completely remove the residual TCA solution, and dried up at room temperature. To each well of the completely dried plate, 100 μl of dye solution, in which 0.4% SRB solution was dissolved, was added to dye the cells for 30 minutes, and the cells were washed with 1% acetic acid to remove excess SRB which was not combined with the cells. The dyed cell plates were dried at room temperature, and 100 μl of 10 mM trisma base solution was added to each well. The solution was mixed by a titer plate shaker for 10 minutes to elute the dye solution. Then, the absorbance at 520 nm was measured by using a microplate reader.

In order to calculate the cyto-toxicity (anti-tumor activity) of the samples on tumor cells, the number of tumor cells at the point of adding the sample (Tz, zero time), the number of cells when only an excess amount of culture medium was added instead of the sample and cultured for 48 hours (C, control), and the number of cells when each concentration of the sample was added and cultured for 48 hours (T, test) were measured respectively. The cyto-toxicity was determined according to the following formulas:

When Tz>T: [(T−Tz)/(C−Tz)]×100

When Tz<T: [(T−Tz)/Tz]×100

From the calculated values thus obtained, $ED_{50}$ (50% effective dose) [the concentration when the sample inhibits 50% of the growth of the tumor cells] was determined by the use of data regression tool of LOTUS program. The $ED_{50}$ value was used as a parameter to determine the intensity of cyto-toxicity of each sample.

Table 15. Results of detection of anti-tumor activity(cyto-toxicity) in vitro

TABLE 15

Results of detection of anti-tumor activity (cyto-toxicity) in vitro

| Sample | $ED_{50}(\mu M)$ | | | | |
|---|---|---|---|---|---|
| | A549 | SK-OV-3 | SK-MEL-2 | XF498 | HCT15 |
| 11 | 40.5 | 8.3 | 11.6 | 37.2 | 10.8 |
| 11-1 | 35.5 | 7.9 | 10.5 | 32.5 | 9.5 |
| 11-2 | 32.1 | 14.0 | 9.9 | 28.4 | 8.7 |
| 11-3 | 10.7 | 1.0 | 3.7 | 3.1 | 0.6 |
| 13'-3 | 28.2 | 27.4 | 8.4 | — | 2.6 |
| 14-3 | 38.3 | 25.6 | 11.0 | 35.4 | 10.6 |
| 14-8 | 51.2 | 12.6 | 14.9 | 45.5 | 13.3 |
| 15-1 | >100 | 39.9 | 14.8 | 59.9 | 11.6 |
| 15-2 | >100 | 25.8 | 12.8 | 45.1 | 20.2 |
| 15-4 | >100 | 21.3 | 12.0 | 55.7 | 11.2 |
| 15-5 | >100 | 35.1 | 16.6 | 60.4 | 12.7 |
| 15-6 | >100 | 19.6 | 10.9 | 40.9 | 10.4 |
| 15-7 | >100 | 38.2 | 14.9 | 63.3 | 15.0 |
| 15-8 | >100 | 24.2 | 10.8 | 55.9 | 12.2 |
| 27-1 | 30.6 | 2.9 | 4.5 | 4.7 | 3.0 |
| 27-2 | 23.5 | 2.7 | 3.8 | 4.1 | 2.4 |
| 27-3 | 36.7 | 3.9 | 9.3 | 11.0 | 4.5 |
| 27-5 | 18.6 | 2.9 | 4.8 | 5.0 | 1.4 |
| 33-1 | 42.8 | 11.5 | 9.3 | 9.8 | 10.4 |
| 33-2 | 44.3 | 24.4 | 14.2 | 16.4 | 17.3 |
| 33-5 | 43.3 | 9.9 | 8.5 | 6.2 | 7.0 |
| 33-6 | 41.4 | 10.6 | 6.9 | 8.7 | 9.3 |
| 35 | 4.6 | 0.3 | 9.1 | 5.5 | 8.7 |
| 35-1 | 10.6 | 13.1 | 12.7 | 11.8 | 12.1 |
| 35-2 | 10.9 | 9.6 | 8.8 | 7.2 | 9.1 |
| 35-3 | 13.1 | 14.6 | 17.9 | 14.0 | 13.9 |

As can be seen from Table 15, the above all samples targeted for the experiments show excellent anti-tumor activity for A549, SK-OV-3, SK-MEL-2, XF498 and HCT15 cell-lines. However, while sample 15-1~15-8 have a little lower activity for A549, SK-OV-3 and XF498 cell-lines, it has remarkably excellent anti-tumor activity for the other cell-lines.

Thus, the present invention provides a thymol derivative having excellent anti-tumor activity.

What is claimed is:

1. A thymol derivative represented by following

Formula 1:

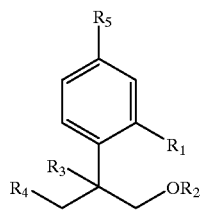

wherein, $R_1$ is a hydroxyl group which may be protected with a acetyl group or isobutyryl group; $R_2$ represents methanesulfonyl, 4-methoxybenzenesulfonyl, 4-nitrobenzenesulfonyl, 4-fluorobenzenesulfonyl, o-toluenesulfonyl, 2-nitro-o-toluenesulfonyl or p-toluenesulfonyl; $R_3$ and $R_4$ together forms an olefin; and $R_5$ represents a methyl group; and pharmaceutically acceptable salts and esters thereof.

2. An anti-cancer agent comprising a thymol derivative represented by Chemical Formula 1 according to claim 1.

* * * * *